US006992313B2

United States Patent
Piestrup

(10) Patent No.: US 6,992,313 B2
(45) Date of Patent: Jan. 31, 2006

(54) X-RAY AND NEUTRON IMAGING

(75) Inventor: Melvin A. Piestrup, Woodside, CA (US)

(73) Assignee: Adelphi Technology Inc., Redwood City, CA (US)

( * ) Notice: Subject to any disclaimer, the term of this patent is extended or adjusted under 35 U.S.C. 154(b) by 223 days.

(21) Appl. No.: 10/246,507

(22) Filed: Sep. 17, 2002

(65) Prior Publication Data

US 2003/0081724 A1 May 1, 2003

Related U.S. Application Data

(60) Provisional application No. 60/376,677, filed on Apr. 29, 2002, provisional application No. 60/322,795, filed on Sep. 17, 2001.

(51) Int. Cl.
*G21K 1/06* (2006.01)
(52) U.S. Cl. .................. 250/505.1; 250/251; 378/145; 378/147
(58) Field of Classification Search ............... 378/145, 378/147, 84, 81; 250/251, 505.1, 573, 570, 250/373
See application file for complete search history.

(56) References Cited

U.S. PATENT DOCUMENTS

| RE28,162 E | * | 9/1974 | Anderson | 396/429 |
| 4,208,088 A | * | 6/1980 | Hunzinger et al. | 359/435 |
| 4,448,499 A | * | 5/1984 | Tokumaru | 359/619 |
| 4,630,902 A | * | 12/1986 | Mochizuki et al. | 359/432 |

* cited by examiner

*Primary Examiner*—Nikita Wells
*Assistant Examiner*—James J. Leybourne
(74) *Attorney, Agent, or Firm*—Joseph Smith

(57) ABSTRACT

An x-ray or neutron apparatus for the transmission of x-ray or neutron images is described, which includes x-ray- or neutron-three-dimensional (3-D) arrays or mosaics, including a plurality of x-ray or neutron lenses positioned so that they form a two-dimensional (2-D) mosaic of compound refractive lenses to provide a plurality of separate x-ray or neutron paths between an object and an image at an x-ray- or neutron-detector. The apparatus is so constructed that it permits separate parts of an object to be imaged such that a total composite image is formed from these various parts. An imaging apparatus of the detection of carcinoma in breast tissue is formed using such an apparatus. Methods of microscopy and imaging are obtained using this apparatus.

26 Claims, 17 Drawing Sheets

X-RAY AND NEUTRON IMAGING

CROSS REFERENCE TO RELATED APPLICATIONS

U.S. Provisional Patent Documents

Nos. 60/322,795 Sep. 17, 2001, M. A. Piestrup, "X-ray and neutron imaging using compound refractive lens arrays."
60/376,677 Apr. 29, 2002, M. A. Piestrup, "X-ray and neutron imaging using compound refractive lens arrays II."

CROSS REFERENCE TO RELATED DOCUMENTS

U.S. Patent Documents

U.S. Pat. No. 6,269,145 B1 May 1998, M. A. Piestrup, R. H. Pantell, J. T. Cremer and H. R. Beguiristain, "Compound Refractive Lens for X-rays," issued: Jul. 31, 2001.
U.S. Pat. No. RE28,162, R. H. Anderson, "Optical apparatus including a pair of mosaics of optical imaging elements," issued Sep. 17, 1974.
U.S. Pat. No. 5,594,773, Toshihisa Tomie, "X-ray Lens" issued Jan. 14, 1997.
U.S. Pat. No. 5,880,478, D. J. Bishop, L. Gammel, and I. P. M. Platzman, Compound Refractive Lenses for Low Energy Neutrons," issued Mar. 9, 1999.
U.S. Pat. No. 6,765,197, H. R. Beguiristain, M. A. Piestrup, R. H. Pantell, "Methods of Imaging, Focusing and Conditioning Neutrons,"(submitted Sep. 27, 2001).

Other Publications

A. Snigirev, V. Kohn, I. Snigireva and B. Lengeler, "A compound refractive lens for focusing high-energy X-rays," Nature 384, 49 (1996).
Yu. I Dudchik, N. N. Kolchevsky, "A microcapillary lens for X-rays, Nuclear Instruments and Methods A421, 361 (1999).
M. A. Piestrup, H. R. Beguiristain, C. K. Gary, J. T. Cremer, and R. H. Pantell "Two-dimensional x-ray focusing from compound lenses made of plastic," Review of Scientific Instruments, 71, 4375 (2000).

STATEMENT REGARDING FEDERALLY SPONSORED R & D

This invention was made with Government support under contract DASG60-00-C-0043 awarded by U.S. Army Space and Missile Defense Command. The Government has certain rights in the invention.

TECHNICAL FIELD

The present invention relates to x-ray or neutron imaging of objects for medical, industrial and scientific applications; for example, it relates to the medical imaging of the human body, and the x-ray or neutron inspection of objects to determine content.

BACKGROUND OF THE INVENTION a. X-ray and Neutron Compound Refractive Lenses

X-rays and neutrons can be collected, collimated, and focused using a series of small-aperture, thin, biconcave lenses with a common optical axis. M. A. Piestrup, J. T. Cremer, R. H. Pantell and H. R. Beguiristain (U.S. Pat. No. 6,269,145 B1, which is incorporated herein by reference), teach that an stack of individual thin unit lenses 12 without a common substrate, but with a common optical axis 10, forms a compound refractive x-ray lens 14, which is capable of collecting and focusing x-rays in a short focal length (as shown in FIG. 1). X-rays and neutrons 45 are focused by the compound refractive lens 14 along an optical axis 10 to a focal point 16. The closely spaced series of $N_x$ bi-concave unit lenses 12 each of focal length $f_1$, result in a focal length f of:

$$f = \frac{f_1}{N_x} = \frac{R}{2N\delta}. \tag{1}$$

The unit lens focal length $f_1$ is given by:

$$f_1 = \frac{R}{2\delta}, \tag{2}$$

where the complex refractive index of the unit lens material is expressed by:

$$n = 1 - \delta + i\left(\frac{\lambda}{4\pi}\right)\mu, \tag{3}$$

R is the radius of curvature of the lens, $\lambda$ is the neutron or x-ray wavelength and $\mu$ is the linear attenuation coefficient of the lens material. For cylindrical unit lenses $R=R_h$, the radius of the cylinder; for spherical lenses $R=R_s$, the radius of the sphere; for the case of parabolic unit lenses $R=R_p$, the radius of curvature at the vertex of the paraboloid.

Equation (1) shows that the total focal length has been reduced by $1/N_x$. The focal length of a single unit lens 12 would be extremely long (e.g. 100 meters), but using 100 of such unit lenses 12 would result in a focal length of only 1 meter. This makes the focusing, collecting and imaging of objects with x-rays and neutrons possible with much shorter focal lengths than was thought possible.

Unfortunately, the aperture of the compound refractive lens is limited. This is due to increased absorption at the edges of the lens as the lens shape may be approximated by a paraboloid of revolution that increases thickness in relation to the square of the distance from the lens axis. These effects make the compound refractive lens act like an iris as well as a lens. For a radius $R=R_h$, $R_s$, or $R_p$, the absorption aperture radius $r_a$ is:

$$r_a = \left(\frac{2R}{\mu N_x}\right)^{\frac{1}{2}} = \left(\frac{4\delta f}{\mu}\right)^{\frac{1}{2}}. \tag{4}$$

If the lenses refract with spherical surfaces, only the central region of the lens approximates the required paraboloid-of-revolution shape of an ideal lens. The parabolic aperture radius $r_p$, where there is a $\pi$ phase change from the phase of an ideal paraboloid of revolution, is given by:

$$r_p = 2((N_x f\delta)^2 \lambda r_i)^{\frac{1}{4}} \approx 2((N_x \delta)^2 f^3 \lambda)^{\frac{1}{4}}, \quad (5)$$

where $r_i$ is the image distance and $\lambda$ is the x-ray wavelength. Rays outside this aperture do not focus at the same point as those inside. The approximation in (5) is true for a source placed at a distance much larger than f.

For imaging, the effective aperture radius $r_e$ is the minimum of the absorption aperture radius, $r_a$, the parabolic aperture radius, $r_p$, and the mechanical aperture radius $r_m$; that is:

$$r_e = MIN(r_a, r_p, r_h). \quad (6)$$

However, since lens shape can be made parabolic and the mechanical aperture can be made larger, the absorption aperture $r_a$ is usually the limiting aperture. For example, using Beryllium as a lens material for x-rays, the absorption aperture is below 1 mm in diameter for x-rays. For cold neutrons the Be lenses are bigger (e.g. 2–4 cm diameter), but the sources are even larger, requiring even larger apertures. Thus the compound refractive lens' apertures are small and limited in their ability to capture the total image or collect most of the flux from sources of neutrons or x-rays.

Since one can always make the mechanical aperture of a lens bigger and, in most cases make the lenses parabolic, the absorption aperture is the dominant determining parameter of the compound refractive lenses aperture size. Note from equation 4, if desire shorter focal lengths f, then the absorption apertures get smaller (e.g. If Kapton is used as the lens material, the absorption aperture for a compound refractive lens is only $2r_a = 100 \, \mu m$ for x-ray photon energies of around 8 keV).

Compound refractive lenses for neutrons and x-rays have been made using a variety of techniques. For focusing and imaging the lenses need to be either bi-concave or plano-concave. They can also be Fresnel lenses with the additional requirement that individual zones need to be aligned accurately as described in U.S. Pat. No. 6,269,145, by M. A. Piestrup et al. The x-ray lenses have been made using compression molding for 2-D lenses (U.S. Pat. No. 6,269,145 B1 May 1998, M. A. Piestrup, R. H. Pantell, J. T. Cremer and H. R. Beguiristain, "Compound Refractive Lens for X-rays,") and drilling for 1-D lenses (U.S. Pat. No. 5,594,773, Toshihisa Tomie, "X-ray Lens"). Bi-concave lenses have been formed by using a capillary filled by epoxy and filled with a series of bubbles: the interface between two bubbles forms a bi-concave lens and a series of such bubbles forms a multi-lens path down the axis of the capillary (Yu. I Dudchik, N. N. Kolchevsky, "A microcapillary lens for X-rays, Nuclear Instruments and Methods A421, 361 (1999)).

b. Visible Optics Arrays of Microlenses

Planar (2-Dimensional, 2-D) optical arrays of microlenses have been used to produce short focal length imaging systems for visible electromagnetic radiation. U.S. Pat. No. Re. 28,162 by R. H. Anderson entitled "Optical Apparatus Including a Pair of Mosaics of Optical Imaging Elements," describes an apparatus which can be used as an image transmission system or a part of a camera's optics for photographing the trace produced on the fluorescent screen of a cathode ray oscilloscope. An optical apparatus is described, which includes two 2-D (or planar) arrays of microlenses forming a plurality of light paths each containing image inverting and erecting elements in different planar arrays (or mosaics), which transmit different portions of an image and recombine such image portions with their original object. A plurality of aperture plates is used to prevent undesired light from reaching the composite image formed on the final image surface, and the lens pairs are spaced so that adjacent image portions partially overlap to provide a single final image.

BRIEF DESCRIPTION SUMMARY OF THE INVENTION

The invention permits the overcoming of the problem of the compound refractive lenses that are highly limited by their apertures and, hence, by their field of view. The method permits the x-ray or neutron imaging of large objects. The invention permits the fabrication of large area arrays of compound refractive lenses that are capable of imaging large objects with either x-rays or neutrons. The invention also permits the collection, focusing or collimation of x-rays or neutrons from large-area sources. The invention permits the use of very small unit lenses of high radius of curvature, which in turn permits short focal length lens systems.

The apparatus is comprised of x-ray- or neutron-three-dimensional (3-D) arrays or mosaics of unit lenses positioned so that they form a two-dimensional (2-D) mosaic of compound refractive lenses to provide a plurality of separate x-ray or neutron paths between an object and an image at an x-ray- or neutron-detector. The x-ray or neutron paths are formed by at least a pair of compound refractive lenses of common optical axes. This pair of compound refractive lenses includes an image-inverting compound refractive lens and an image-erecting compound refractive lens in the two different 2-D mosaics. Each set of 3-D arrays is supported in proper spaced relationship with respect to each other and said object and image, so that different image portions of the image of said object are combined at the surface of said detector in focus and with their original relative orientations. In addition the compound refractive lenses are spaced from each other inside the 3-D arrays for directing the viewing fields of the pairs of said compound refractive lenses so that said image portions partially overlap and the overlapping areas of the image portions coincide with each other at the detector surface to form a final composite image, which is a complete reproduction of the image of said object.

DETAILED DESCRIPTION OF THE PREFERRED EMBODIMENTS

1. Three-dimensional (3-D) Lens Array

Figure 1:
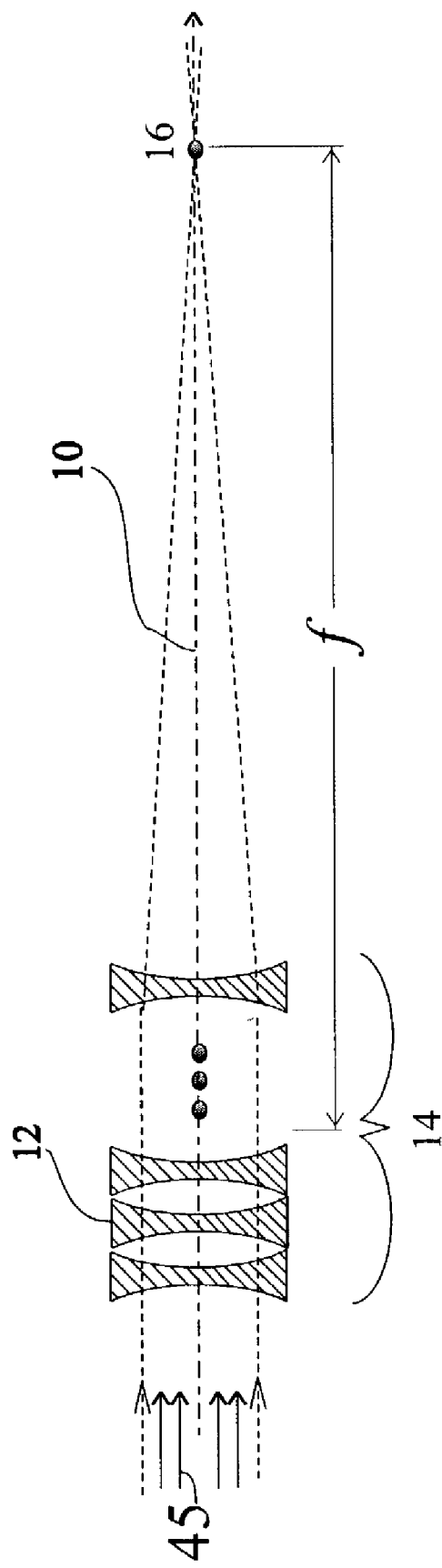
FIG. 1 shows a side view of the prior art compound refractive lens.
Figure 2:
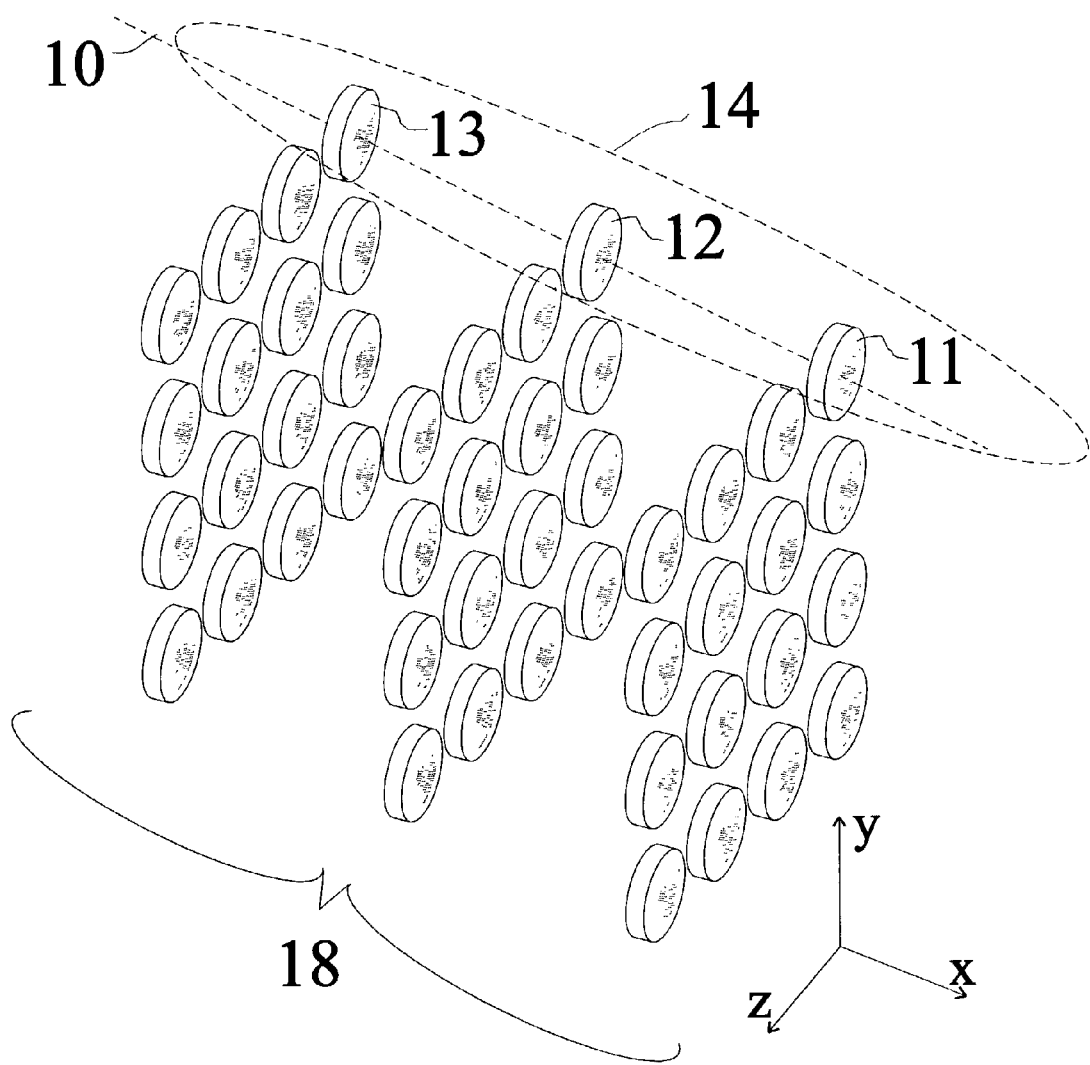
FIG. 2 shows an exploded view of a 3-D lens array

To increase the area of collection and imaging, 3-D arrays of unit lenses are used. FIG. 2 shows a partial solution and a fundamental component: the three dimensional (3-D) array of unit lenses. Arrays of concave unit lenses are aligned in rows and columns. The unit lenses 11, 12, and 13 are aligned so that the optical axis 10 of each is coaxial with succeeding unit convex lenses, forming a compound refractive lens 14. Identical compound refractive lenses are repeated in the y and z directions forming a 3-D lens array 18. Each compound refractive lens is capable of transporting x-rays or neutrons for collection, collimation, or imaging. The total number of unit lenses $N_t$ is given by product of $N_x$, $N_y$ and $N_z$, where $N_x$ is the number of unit lenses in the x-direction, $N_y$ is the number in y-direction, and $N_z$ is the number in the z direction. Thus, $N_t = N_x N_y N_z$.

A single 3-D array can be used for collection of x-ray or neutrons. Such an array would produce $N_y \times N_z$ focused microbeams if used to image a source of x-rays or neutrons. As discussed in section 4.4, this can be used for simple collection of x-ray or neutrons.

Figure 3:
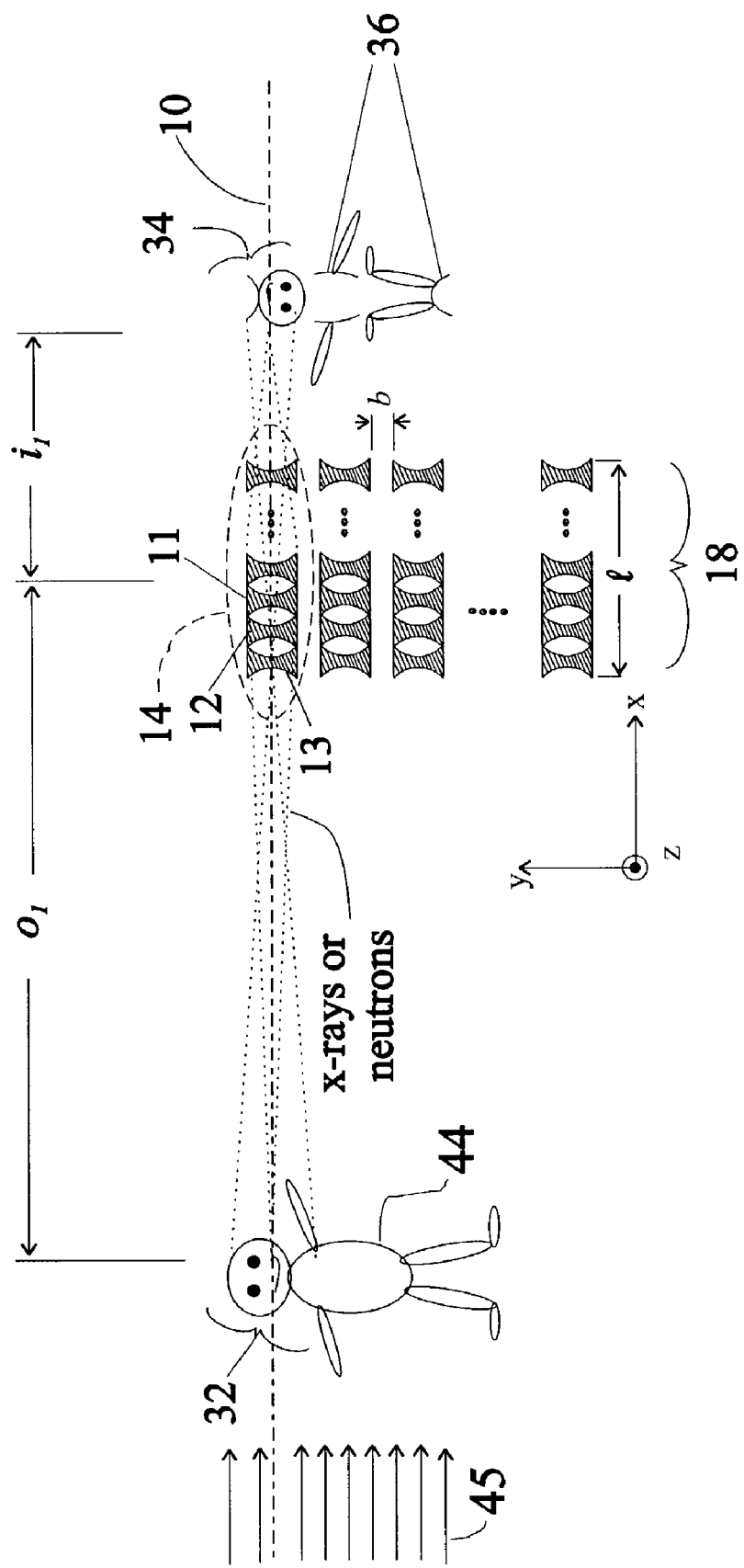
FIG. 3 shows a side view of a single 3-D lens array that gives partial inverted images of an object using neutrons or x-rays.

However, if one wishes to obtain a complete image, such a single 3-D array is only a partial solution to the problem of small aperture size, as FIG. 3 demonstrates. The 3-D lens array in FIG. 3 is presented in only a planar cut for ease in visualization. The array 18 of FIG. 3 is the same as the array 18 in FIG. 2. An object 44 in FIG. 3 is illuminated by x-rays or neutrons 45. The compound refractive lens 14 images part of the object (i.e. the head of the man) 32 to a point on the other side of the compound refractive lens 14. The partial image 34 is inverted and has been de-magnified as shown in the figure. Each compound refractive lens (e.g. 14) obeys the lens formula:

$$\frac{1}{o_1} + \frac{1}{i_1} = \frac{1}{f}, \quad (7)$$

where $o_1$ is the object distance and $i_1$ is the image distance as shown in FIG. 3. The image is de-magnified by:

$$M = \frac{i_1}{o_1} \quad (8)$$

Each succeeding compound refractive lens in the y and z directions will image a small section of the object (e.g. 32). However, each partial image (e.g. 34) is inverted and overlaps other images (e.g. 36). Thus, using the 3-D array of compound refractive lenses 18 will only produce multiple, inverted, overlapping images 36 (i.e. the total image is scrambled and blurred).

2. One-to-One Imaging

Figure 4:
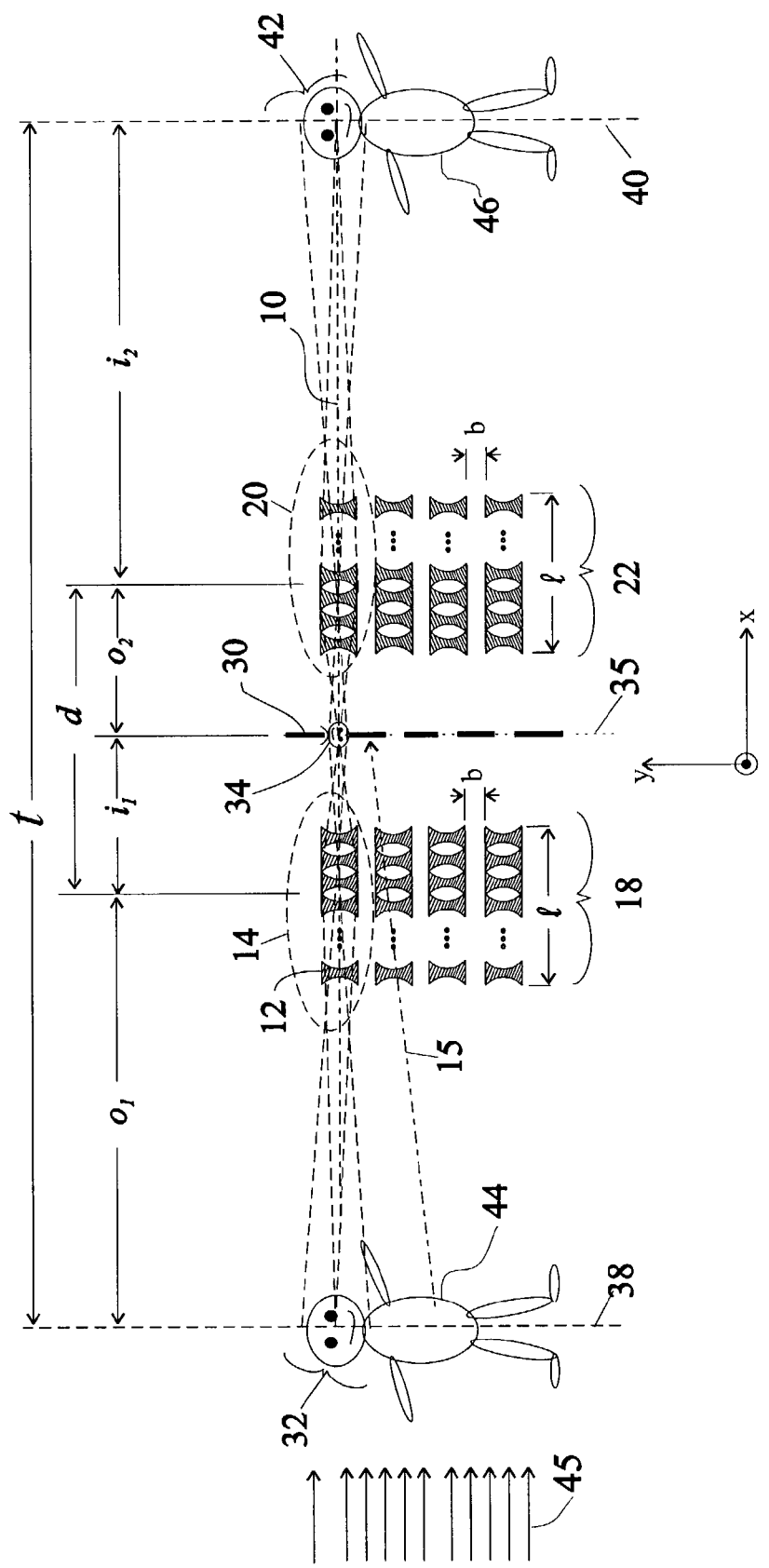
FIG. 4 shows a side view of 3-D lens array system that gives a one-to-one image of an object using neutrons or x-rays.

As shown in FIG. 4, to produce a complete composite image 46 of the object 44 we must use another 3-D lens array 22 (called the erecting 3-D lens array). In this embodiment, a one-to-one image is produced (i.e. the object 44 is the same size as the produced image 46). The erecting 3-D lens array 22 matches those of 18 (now called the inverting 3-D lens array). Each inverting compound refractive lens 14 and erecting compound refractive lens 20 of the two 3-D lens arrays has a common optical axis 10. Compound refractive lens 14 forms an inverted, intermediate partial image 34 of part of the object 32 (i.e. the head of the man in FIG. 4) at an aperture stop 30. The second compound refractive lens 20 erects the intermediate image 34 and places the resulting final partial image 42 in partially overlapped registration with adjacent images, forming an erect uniform composite image 46 in the image plane 40 of the whole object 44 from the object plane 38. For this embodiment, distances $i_1 = o_2$ and $i_2 = o_1$. The separation between the erecting 3-D lens array 18 and the inverting 3-D lens array 22 is $d = i_1 + o_2 = 2i_1$. In FIG. 4, it is assumed that the lengths l of 3-D lens arrays 18 and 22 are very small compared to the 3-D lens array focal lengths f. This permits the use of the simple thin-lens formulas (7) and (8).

To form a single complete image, the viewing fields of each of the adjacent compound refractive lenses must overlap on the object plane 38 so that the image portions transmitted through such adjacent compound lens pairs have partially overlapping areas in which multiple image points of a common object point must coincide on the image plane 40 where they are in focus. The field of the object for each compound refractive lens pairs and the field of coverage of the resulting image portion extend, approximately, to the optic axes of the adjacent lens pairs. Since multiple images of each object point are formed, there is overlapping in the composite image. When an object is imaged through two or more parallel compound refractive lenses, several conditions must be satisfied in order to obtain coincidence of the multiple images of each object point in the final image. (1) A correspondence between each point in the object plane must be made to each point in the image plane. (2) Brightness uniformity of the final image is obtained by having a large amount of overlap of the individual image fields of adjacent compound refractive lens-pairs and by providing a gradual tapering off of the field's brightness toward the edge of each image, by vignetting, so that sharply defined image field edges do not appear. (3) The two compound refractive lenses are spaced such that there is an intermediate image between them.

As shown in FIG. 4, each of the 3-D lens arrays 18 and 22 is composed of a plurality of unit concave lenses, forming a two-dimensional array of compound refractive lenses that can be spaced apart (in the y and z directions) by approximately the same distance, b, which can be approximately equal to the effective aperture radius (i.e. equation 6) of one compound refractive lens (i.e. b≈$r_e$). This provides uniform coverage of the object plane 18. The spacing between CRLs b can be larger but is limited by the field of view of each CRL, which is determined in part by its length l. As discussed above, the best selection of the effective aperture radius is the absorption aperture radius $r_e \approx r_a$.

As one skilled in the art will readily see, the separation between compound refractive lenses in the y and z directions can also vary appreciably without undue loss of image quality. The important design principles to follow are given by conditions (1) and (2) above to achieve a uniform brightness and a clear total image. The field of view of a CRL should be taken under consideration in determining the spacing b between CRLs in the 3D arrays. The field of views of adjacent CRLs must overlap such that the final images produced are overlapping and have uniform brightness. The field of view of a CRL is determined primarily by its focal length f and its physical length l. If l is on the same order as the focal length f, then a thick lens analysis of the CRL should be done to determine the field of view. An estimate of the field of view can be made by assuming that the CRL optically acts like a pipe or cylindrical tube of diameter $r_a$ and length l. The field of view is then limited by the aspect ratio of the tube (i.e. $l/2r_a$). For l≦0.5f the field of view (FOV) is roughly given by FOV≈$4r_a o/l$, where o is the distance from the object to the center of CRL, FOV is the full width half maximum of the transmitted flux and $r_a$ is given by equation (4). The spacing between the lenses b is then given by $$b \approx 2\left(2\frac{o}{l} - 1\right)r_a,$$

where again we are assuming that the effective aperture is given by the absorption aperture, $r_e \approx r_a$. For longer lenses (l>0.5f) the formula is less accurate but still useful for estimating b.

The length and positioning of the 3-D lens arrays can be obtained by solving the lens equation (7) for the two lenses and by the fact that $i_1 = o_2$, $o_1 = i_2$. The separation d between the lenses is given by $d = i_1 + o_2 = 2i_1$ and the total length of the 2-D lens system (from object plane to image plane) $t = (o_1 + i_1 + o_2 + i_2) = 2(i_1 + o_1)$. Solving for the normalized total length (with the focal length f), T=t/f in terms of the normalized lens separation D=d/f.

$$T = D + \frac{2D}{D-2} \quad (9)$$

Figure 5:
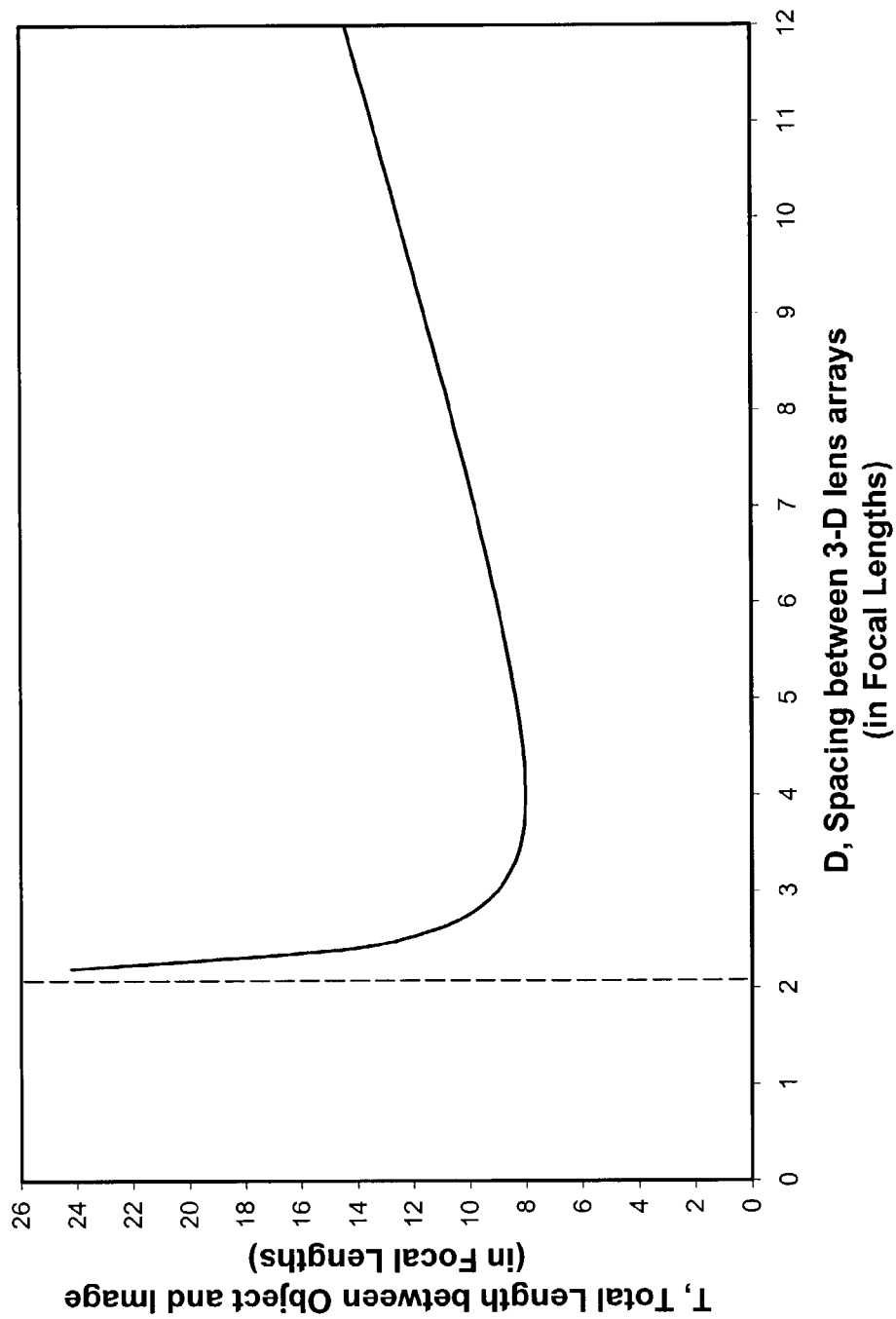
FIG. 5 shows a plot of the total length between an object and image (in focal lengths) as a function of the spacing between 3-D lens arrays (in focal lengths).

As shown in FIG. 5, plotting the total normalized length T as a function of spacing between the inverting and erecting 3-D lens arrays D gives the parameter range for the positioning of the lenses. From FIG. 5 the minimum length is t=8f (or 8 focal lengths) with d=4f (lens separation is 4 focal lengths). For example, if the compound refractive lenses' focal lengths of the 3-D lens arrays are designed to be f=25 cm, then t=200 cm, d=100 cm, and $o_1 = i_1 = o_2 = i_2 = 50$ cm, giving the minimum lens system length (from object-to-image planes). As FIG. 5 shows, other parameter ranges are possible. The design must include the required overlap of images and the required uniformity of brightness.

Bi-concave unit lenses 12 are being used in the 3-D lens arrays 18 and 22. Other conventional unit lenses can be used such as plano-concave and Fresnel lenses.

In FIG. 4, the aperture stop 30 acts as a block for stray rays (e.g. "cross talk" ray 15) coming from other adjacent compound refractive lenses. These stray rays would blur the image and produce a noise background to the true image 46. A single central aperture stop is used in this embodiment; other aperture stops can be strategically placed on either side of the 3-D lens arrays to prevent stray rays (x-rays or neutrons) from entering the wrong field. Multiple apertures are shown in FIGS. 15 and 16 and discussed below.

In summary, the embodiment of FIG. 4 gives one-to-one focusing (no change in image size relative to the object size). In this embodiment, the two compound refractive lens arrays 18 and 22 are identical, having identical focal lengths and symmetrical spacing. The spacing between the lenses is $d = i_1 + o_2 = 2i_1$. This embodiment can be used for medical imaging to replace ordinary radiographs. Since the 3-D lens system will have a depth of focus, one can image into the interior of the human body at a particular depth.

2. Magnified Imaging

Figure 6:
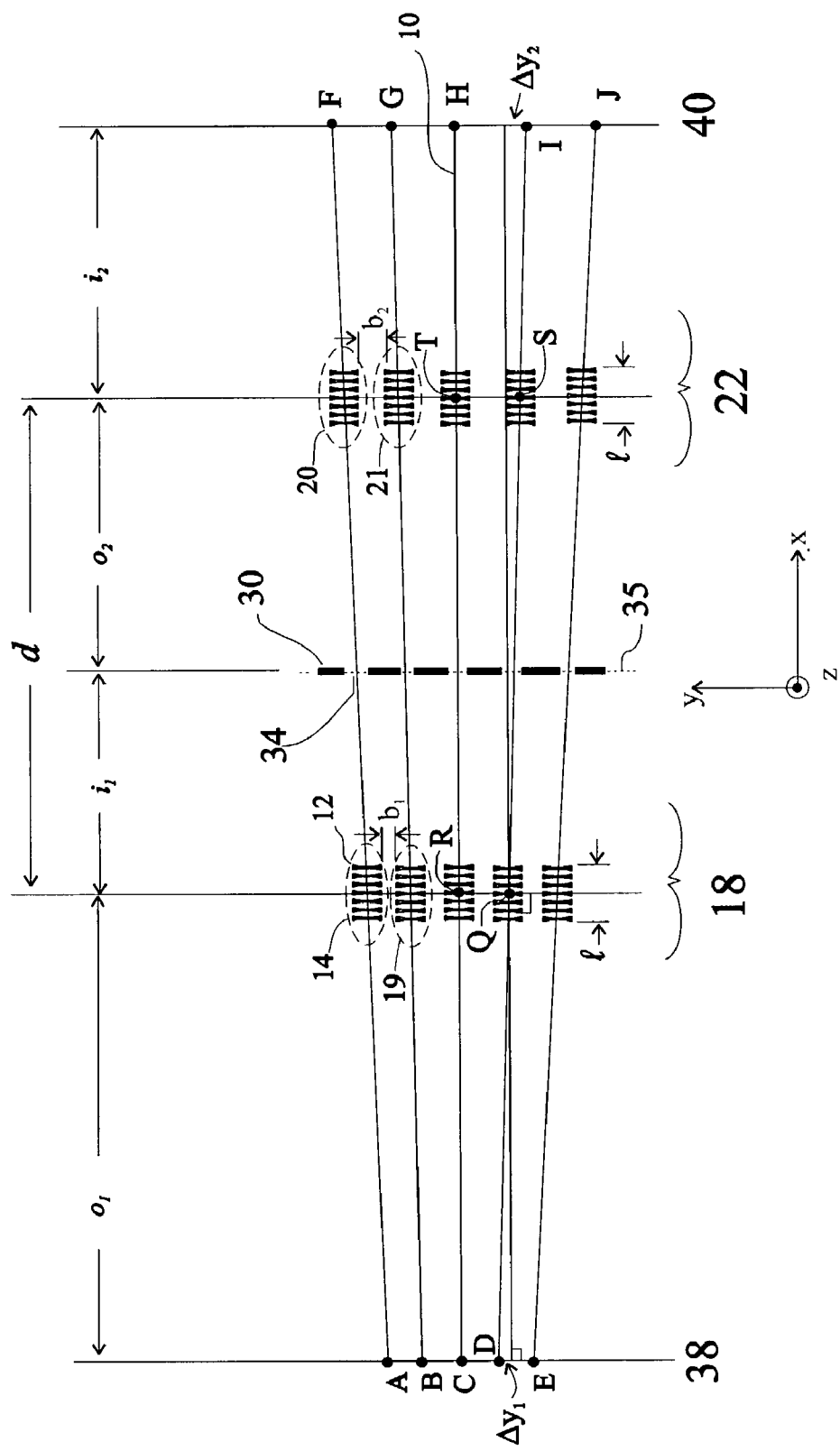
FIG. 6 shows a side view of 3-D lens array system using thin compound refractive lenses that produces a magnified image of an object.

To obtain a magnified image we must use two different inverting and erecting 3-D lens arrays 18 and 22 as shown in FIG. 6. Unlike the one-to-one imaging system, the inverting 3-D lens array 18 is different from the erecting 3-D lens array 22 in that the separation $b_1$ between compound refractive lenses 14 and 19 of the inverting 3-D array 18, is different than the separate $b_2$ of compound refractive lenses 20 and 21 of the erecting 3-D lens array 22. (Indeed, the focal lengths of these two lens arrays 18 and 22 can be different). These separations, $b_1$ and $b_2$, are repeated in the compound refractive lens arrays in the y and z directions. As before, the inverting compound refractive lens (e.g. 14) and erecting compound refractive lens (e.g. 20) have a common optical axis AF. Again the physical lengths, l, of the compound refractive lenses (e.g. 14, 19, 20, 21) forming the 3-D lens arrays are much smaller than their respective focal length's f. In the dimensions perpendicular to AF (i.e. the y-direction), the compound refractive lenses form a 3-D array, each of which has the same focal length and mechanical and absorption apertures. The inverting 3-D lens array 18 positioned closest to an object plane AE, 38, transmits the image of the object plane 38 onto a central image plane 35 as the inverted intermediate image portions (e.g. 34). The erecting lens 3-D lens array 22 transmits the inverted intermediate image 22 in focus onto an image plane FJ, 40, as an erected final image of the same orientation as the image of the object. Thus, it can be seen that a compound-refractive lens 14 on the inverting 3-D lens array 18 and a compound-refractive lens 20 on the erecting 3-D lens array 22 form a compound-refractive-lens pair which act together as an lens train which transmits a portion of the image of an object located in the object plane 38 onto the image plane 40 as an erected image portion of the same orientation as the corresponding object portion. The final image can be magnified or de-magnified depending on selection of spacing and focal length of the lens system. How these parameters are selected is discussed next.

The principles of operation of the 3-D lens system will be discussed in reference to FIG. 6. The diverging optical axis of FIG. 6 illustrates the general case in which spacing between compound refractive lenses differs in the two 3-D arrays. However, the rules for determining the dimensional relationship between the two 3-D arrays are the same for the other cases of either converging or parallel optical axes, resulting in demagnification or no-magnification, respectively. The total magnification of the overall 3-D lens system must be equal to the product of the magnification of the two inverting and erecting 3-D compound refractive lenses (e.g. 14 and 20) in order to obtain coincidence of overlapping image portions and focus each portion in the same plane, which is necessary to form a complete image.

We will use the same terminology as taught by R. H. Anderson to explain the 3-D lens array operation. A grid of imaginary lines is formed such that each intersection or node of the grid lies on an optical axis of one of the compound refractive lenses. In FIG. 6 points A, B, C, D, and E represent nodes in the object plane 38. The grid or latticework in the object plane is imaged onto the image plane 40. Points A, B, C, D, and E are imaged on to points F, G, H, I, and J in the image plane. "Lattice magnification" $M_L$ is defined as the ratio of size of the object in the object plane 38 divided by the size of its image in the image plane 40. Thus, the length AE will be lattice magnified to FJ.

"Nodal magnification" $M_n$ is defined as the total magnification of a compound refractive lens pair for the limited object portion covered by said compound refractive lens pair. This nodal magnification is the product of the magnification of the two compound refractive lenses (e.g. 14, 20) that lie along the same optical axis.

For the complete 3-D lens system to work, the lattice magnification $M_L$ must equal the nodal magnification, $M_n$, ($M_L=M_n$). This is equivalent to saying separate image portions will coincide and overlap if the size of each image portion has been magnified by the same amount as the spacing between the image portions.

In the simplest analysis, the compound refractive lenses are assumed to be thin {i.e. their total lengths l are much less than their focal lengths (l<<f)}. This permits the compound refractive lenses to be represented by single points (e.g. R and Q for the inverting compound refractive lenses 14 and S and T for the erecting compound refractive lenses 20). This gives a very simple analysis to determine the geometry of the 3-D lens system. Using the simple planar geometry, the distances between the compound refractive lenses is given by:

$$M_L = \frac{RQ + RH\left(\frac{TS-RQ}{RT}\right)}{RQ - CR\left(\frac{TS-RQ}{RT}\right)} \qquad (10)$$

The nodal magnifications of the compound refractive lenses 14 and 20 are given for each lens as:

$$M_1 = \frac{UV}{CD} = \frac{i_1}{o_1}, M_2 = \frac{HI}{UV} = \frac{i_2}{o_2} \qquad (11)$$

The nodal magnification is given by a product of the two compound refractive lenses:

$$M_n = M_1 \cdot M_2 \qquad (12)$$

For complete image formation without distortion $M_n=M_L$ or using equations (10–12):

$$M_1 \cdot M_2 = \frac{i_1}{o_1} \cdot \frac{i_2}{o_2} = \frac{RQ + RH\left(\frac{TS-RQ}{RT}\right)}{RQ - CR\left(\frac{TS-RQ}{RT}\right)} \qquad (13)$$

This equation can be put into a more convenient form. If the distance between the lenses is given by $d=i_1+o_2$, the ratio of the distances between inverting and erecting compound refractive lenses is given by:

$$\Delta = \frac{TS}{RQ} \qquad (14)$$

Rearranging equation (13) we have:

$$\Delta = 1 + \frac{(M_n - 1)}{d + i_2 - M_n o_1} \qquad (15)$$

Equation (12) or (15) can be used to design the 3-D lens systems for x-ray and neutron large area imaging and collection. These two equations give the lens spacing, which must be satisfied to form the complete reconstructed image using the compound refractive lens system as given in FIG. 6. Equation (15) shows that the ratio of the compound refractive lens separation is given by the nodal magnification $M_n$, lens separation d and image distance $i_2$ from the second lens and object distance $o_1$ from the first lens.

In the middle between the 3-D lens arrays (e.g. 3-D lens arrays 18 and 22 in FIG. 4, and FIG. 6) is an accurately aligned array of apertures or "field stops" 30 capable of passing x-ray and neutrons only at the aperture of the iris. Known as a "field stop" in visible optics, this array of apertures 30 functions to limit "cross talk" between images and prevents multiple images. A single central aperture stop is used in this embodiment; other aperture stops can be strategically placed on either side of the 3-D lens arrays 18 and 22 to prevent stray rays (x-rays or neutrons) from entering the wrong field.

In the literature, the compound refractive lenses have apertures that limit the useful collection area. There are three possible apertures that limit the lenses' size. These are the ordinary mechanical aperture, the absorption aperture and the parabolic aperture. The absorption and mechanical apertures can be useful in that they can attenuate the scattered x-rays, preventing skewed rays from passing through any two compound refractive lenses which are not on the same optical axis. The "field-stop" or aperture array and the absorption and mechanical aperture are designed to prevent unintended combinations of compound refractive lenses from passing rays (neutron or x-rays) that result in spurious images or multiple images or stray rays of x-rays or neutrons.

Figure 7:
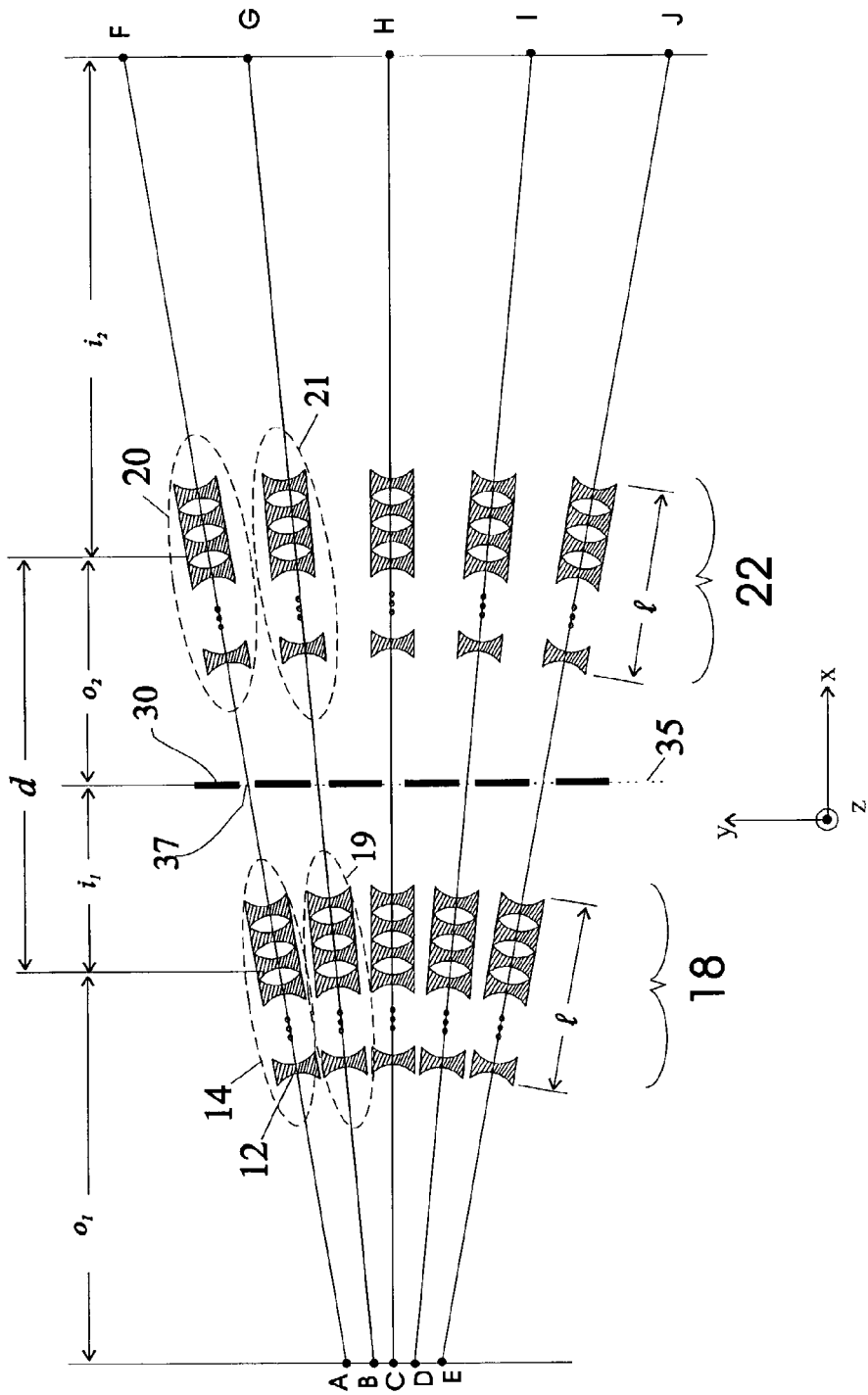
FIG. 7 shows a side a side view of 3-D lens array system using thick compound refractive lenses that produces a magnified image of an object.

If the focal lengths, f, and the lengths, l, of the compound refractive lenses are similar in size, "thick-lens" design theory, as given in the literature of visible optics, must be used and the separation between unit compound lenses must change continuously in the y and z direction. This is shown in FIG. 7. The compound refractive lenses 14 and 19 (and 20 and 21) slope away from one another. The slope is the same for both sets of lenses, but as before, 14 and 19 have the same optical axis AF. To accommodate this change in slope, the spacing between unit lenses must change as one travels along the optical axis. The slope should follow equation (15).

Figure 8A:
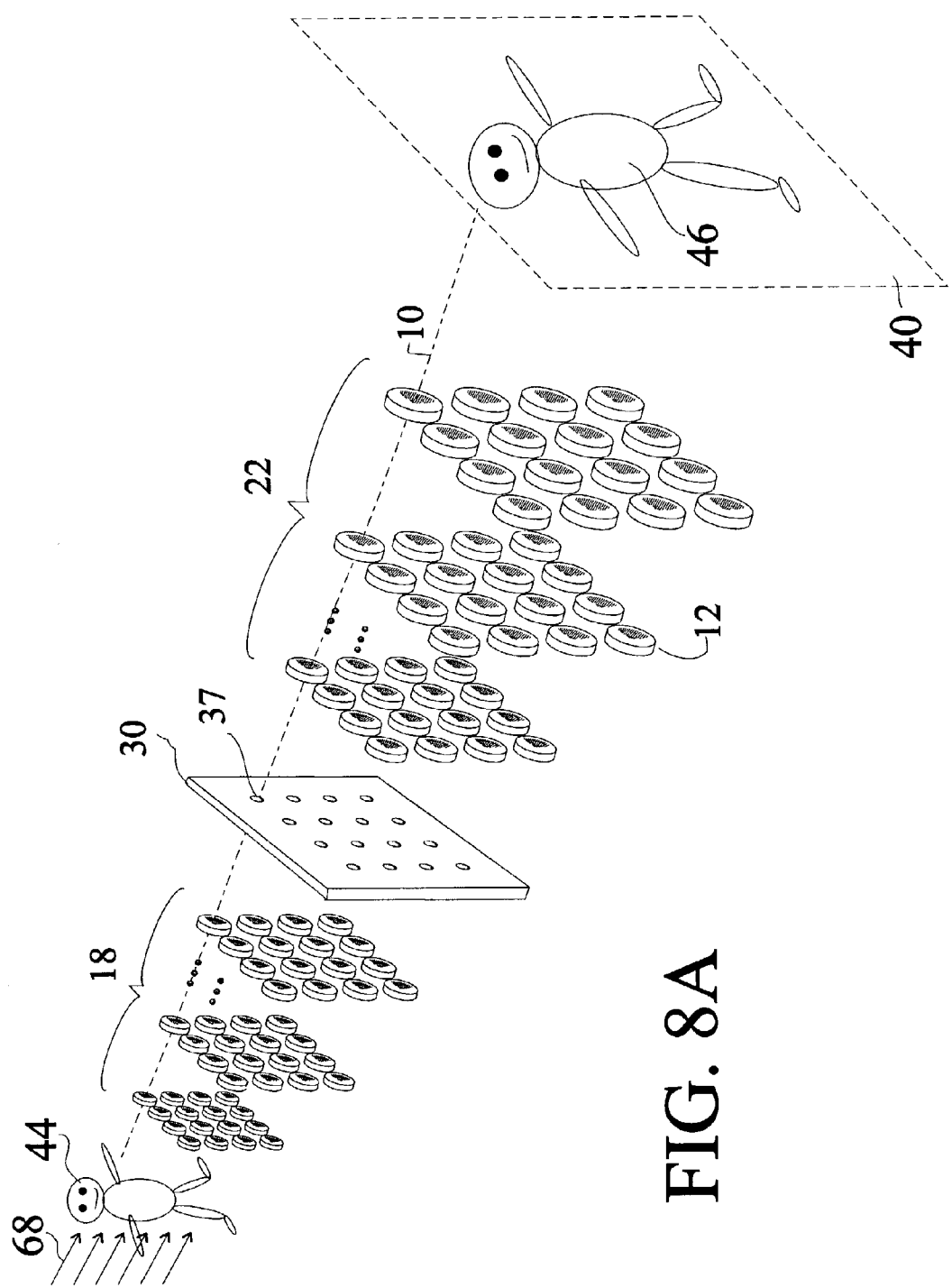
FIG. 8A shows an exploded view of 3-D lens array system that produces a magnified image of an object.

A exploded view of a projection x-ray imaging system that gives an magnified image 46 of the object 44 using the 3-D lens system of FIG. 7 is shown in FIG. 8A. The exploded view shows a 3-D drawing of this embodiment. The inverting 3-D lens array 18 positioned closest to an object 44 transmits an image into an aperture 37 (of the aperture array 30) as the inverted intermediate image portions. The erecting lens 3-D lens array 22 transmits the inverted intermediate image in focus onto an image plane 40, as an erected final image 46 of the same orientation as the image of the object. Unit lenses forming the compound refractive lenses in the x-direction have a common optical axis 10.

Figure 8B:
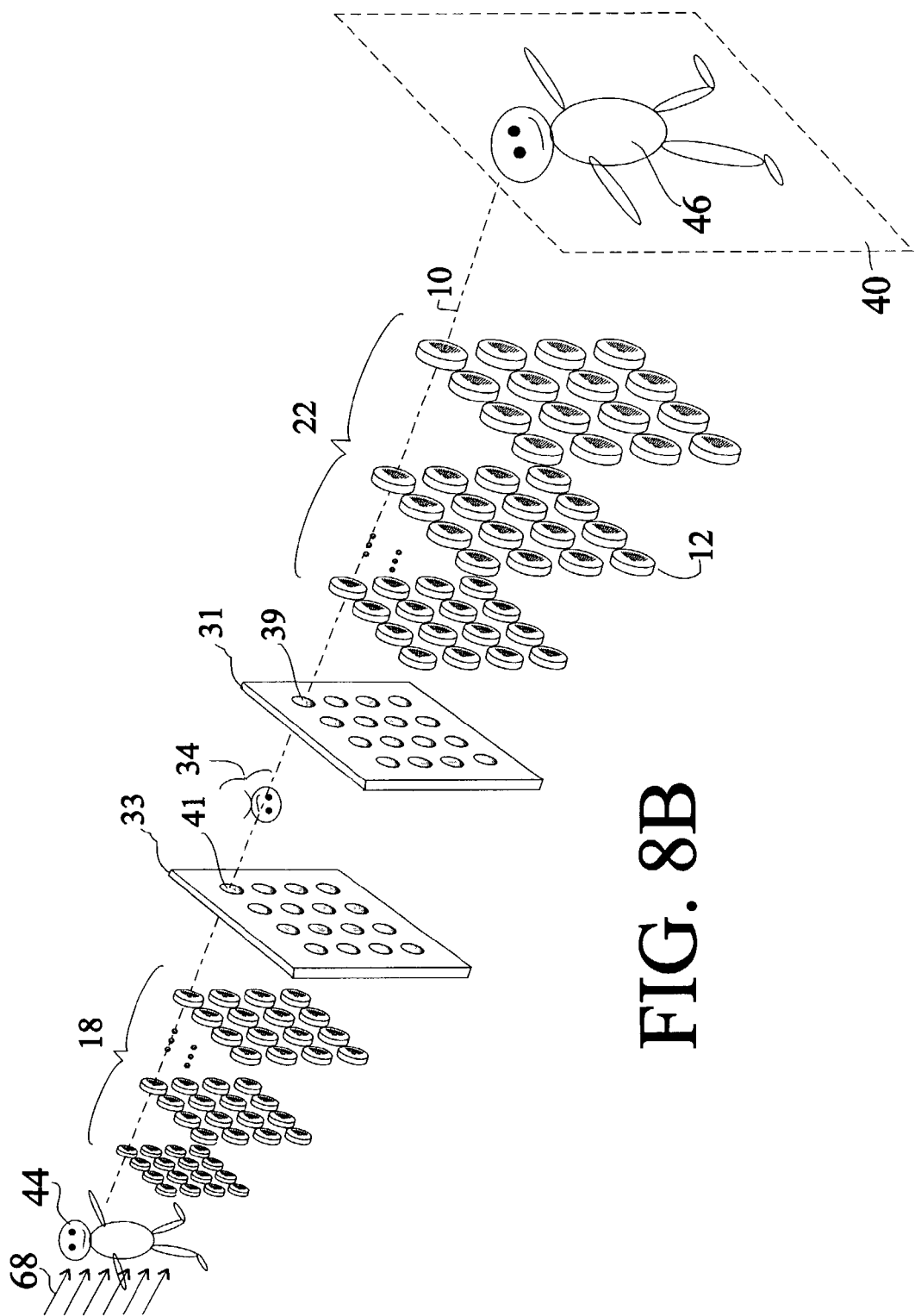
FIG. 8B shows an exploded view of 3-D lens array system with two field stops that produces a magnified image of an object.

In embodiments of FIG. 8A only one "field stop" or aperture array is used. Multiple "field stops" or aperture arrays can be used to improve the minimization of cross talk between images. Field stops or aperture arrays are made of either x-ray or neutron absorbing materials (e.g. lead of x-rays and Cd for neutrons) depending upon if the apparatus is designed for neutrons or x-rays. As shown in FIG. 8B, in the middle between the 3-D lens arrays (e.g. 18 and 22 in FIG. 8B) are two accurately aligned arrays of apertures or "field stops" 31 and 33 capable of passing x-ray and neutrons only at the aperture of the iris. The partial inverted image 34 is in between field stops 31 and 33. These field stops can be placed so that the apertures (e.g. 41 and 39) can be of a reasonable size and still block stray x-rays. These apertures 41 and 39 are aligned with the optical axis of each set of CRLs in the 3-D arrays 18 and 22. The apparatus here is identical to the apparatus of FIG. 8A with the exception that two aperture arrays 33 and 31 are used (a first array of apertures 33 and a second array of apertures 31). The inverting 3-D lens array 18 positioned closest to an object 44 transmits an image into the first aperture 41 (of the first aperture array 33) and then on to the second aperture 39 (of the second aperture array 31). The partial intermediate image is formed between the two aperture arrays 33 and 31. The erecting lens 3-D lens array 22 transmits the inverted intermediate image in focus onto an image plane 40, as an erected final image 46 of the same orientation as the image of the object. Unit lenses forming the compound refractive lenses in the x-direction and the two apertures 41 and 39 have a common optical axis 10.

Figure 8C:
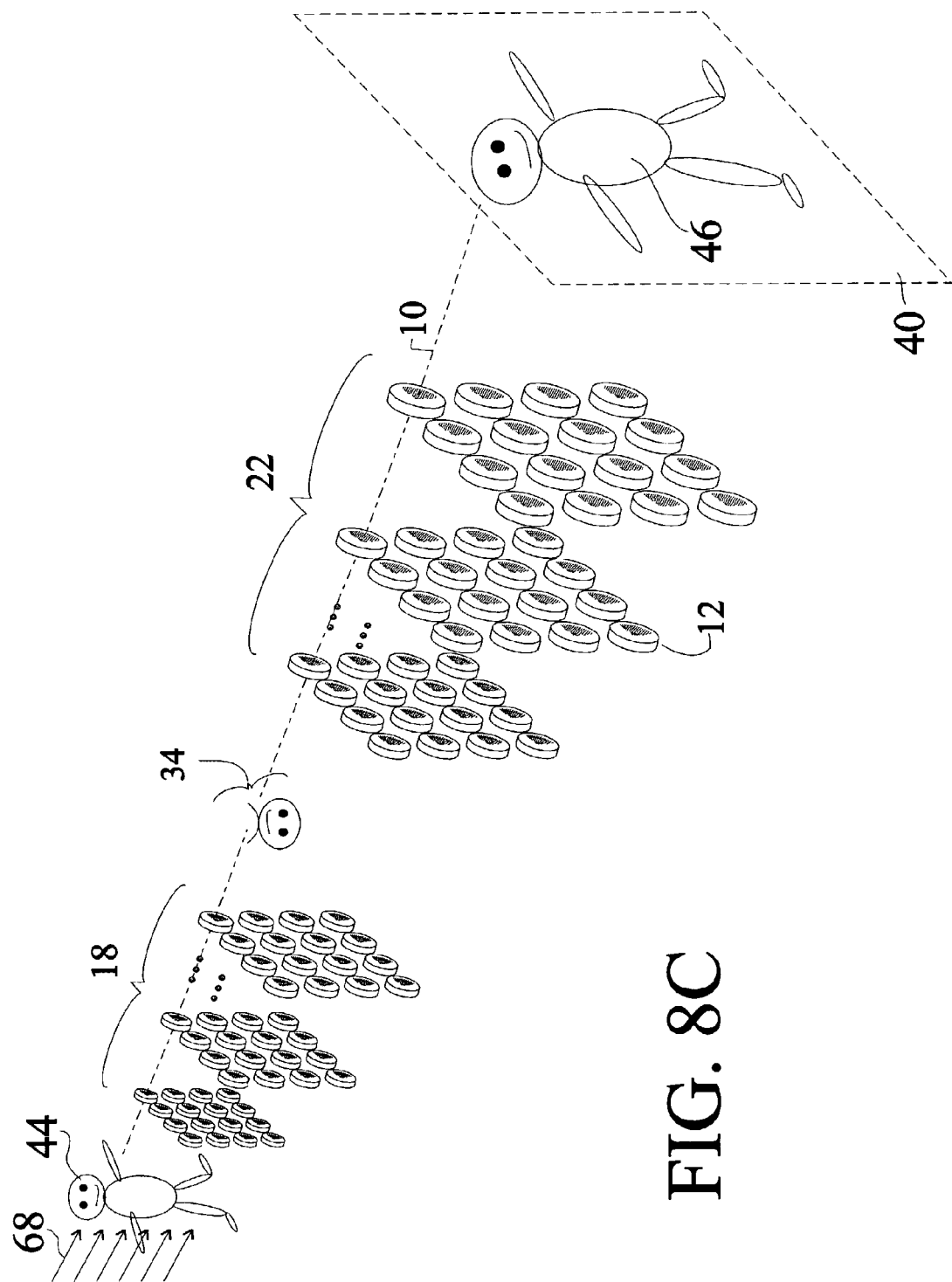
FIG. 8C shows an exploded view of 3-D lens array system that uses the limited field of view of the CRLs and produces a magnified image of an object.

In a preferred embodiment of FIG. 8C no field stop or aperture array need be used. This is because the CRLs are self-apertured and have a limited field of view. The spacing between the lenses (b of FIG. 4 and $b_1$ and $b_2$ of FIG. 6) must be adjusted such that the various fields of view overlap at the half-power points and that there is no cross-talked between the adjacent CRLs (e.g. ray 15 passing through erecting CRL 20 in FIG. 4). As stated before, the spacing between lenses must also be adjusted so that the lattice magnification $M_L$ must equal the nodal magnification, $M_n$, ($M_L=M_n$).

Figure 8D:
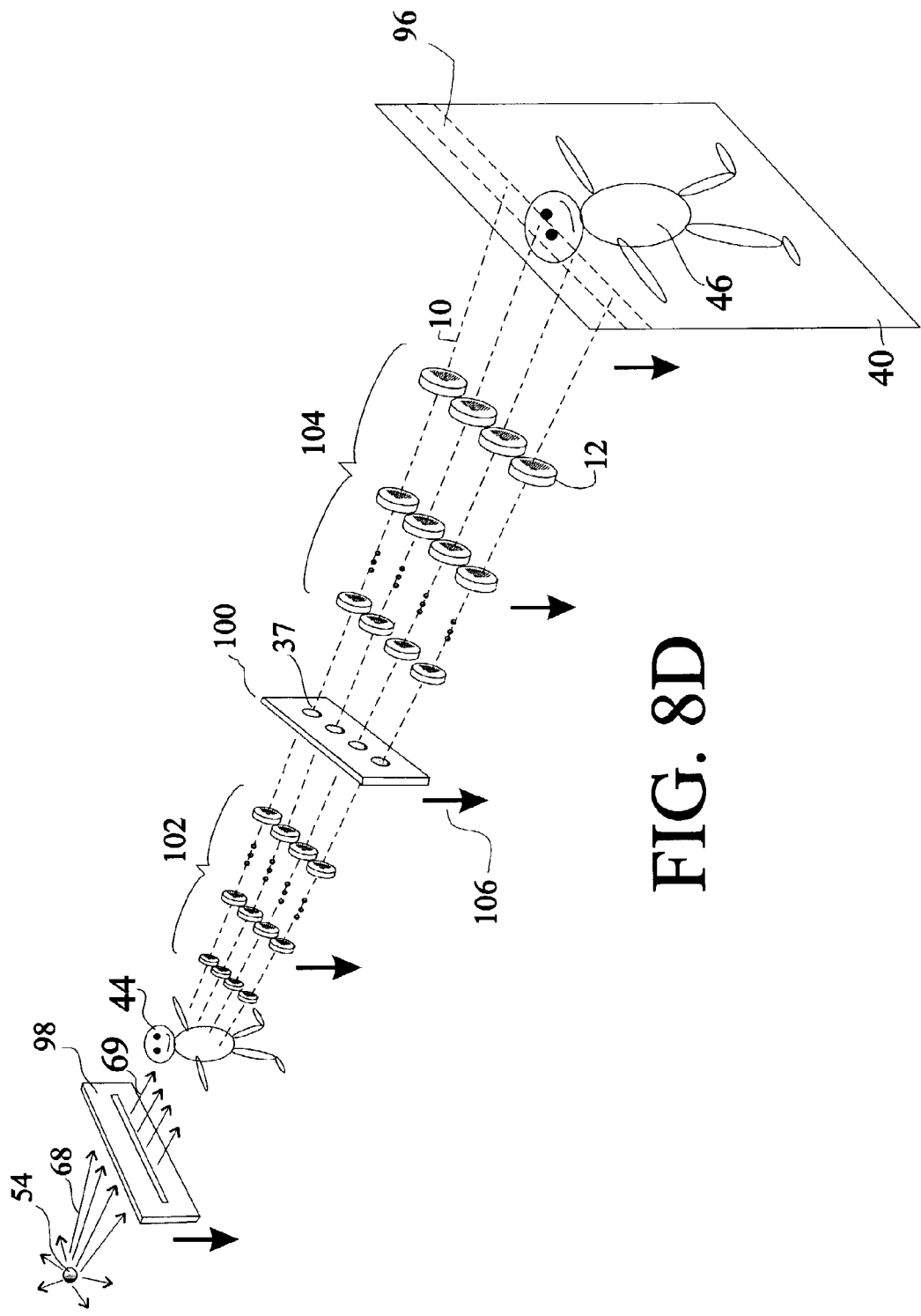
FIG. 8D shows an exploded view of a scanning 2-D lens array system that produces a magnified image of an object.

In another embodiment shown in FIG. 8D of the x-ray or neutron imaging apparatus, 2-D optical arrays and field stops 100 and 102 are moved together transversely to scan the object 44 and form a complete image 46 of a larger object 44 than the aperture field of the lens system. An exploded view of a projection x-ray imaging system that produces a complete composite image 46 of the object 44 using the 2-D lens system is shown in FIG. 16. The exploded view shows a 3-D drawing of this embodiment. The inverting 2-D lens array 104 positioned closest to an object 44 transmits an image into an aperture 41 (of the aperture array 100) as the inverted intermediate image portions. The erecting lens 3-D lens array 22 transmits the inverted intermediate image in focus onto an image plane 40, as an erected final image 46 of the same orientation as the image of the object. Unit lenses forming the compound refractive lenses in the x-direction have a common optical axis 10.

In the embodiment of FIG. 8D, an x-ray source 54 is provided with a slit aperture 98 which scans with the 2-D lens arrays 102 and 104 and the 1-D field stop 100. As one skilled in the art knows, these components 98, 100, 102 and 104 can be attached by an aluminum plate or other means (not shown) that ties all four elements together for rigidity and optical alignment such that the optical axes (e.g. 10) remain fixed relative to the elements and can be scanned in the direction 106 such that the slit image (or rectangular illuminated area of the image) 96 is formed and scanned in the direction 106 to produce a complete composite image 44 of the object 44. Other methods for scanning these elements and holding them optically rigid relative to one another are known to those skilled in the art.

The total number of unit lenses can be roughly determined by the following analysis. The number of unit lenses for particular focal length f in the transverse (i.e. x-direction) can be determined from equation (1):

$$N_x = \frac{R}{2f\delta} \quad (16)$$

Figure 9:
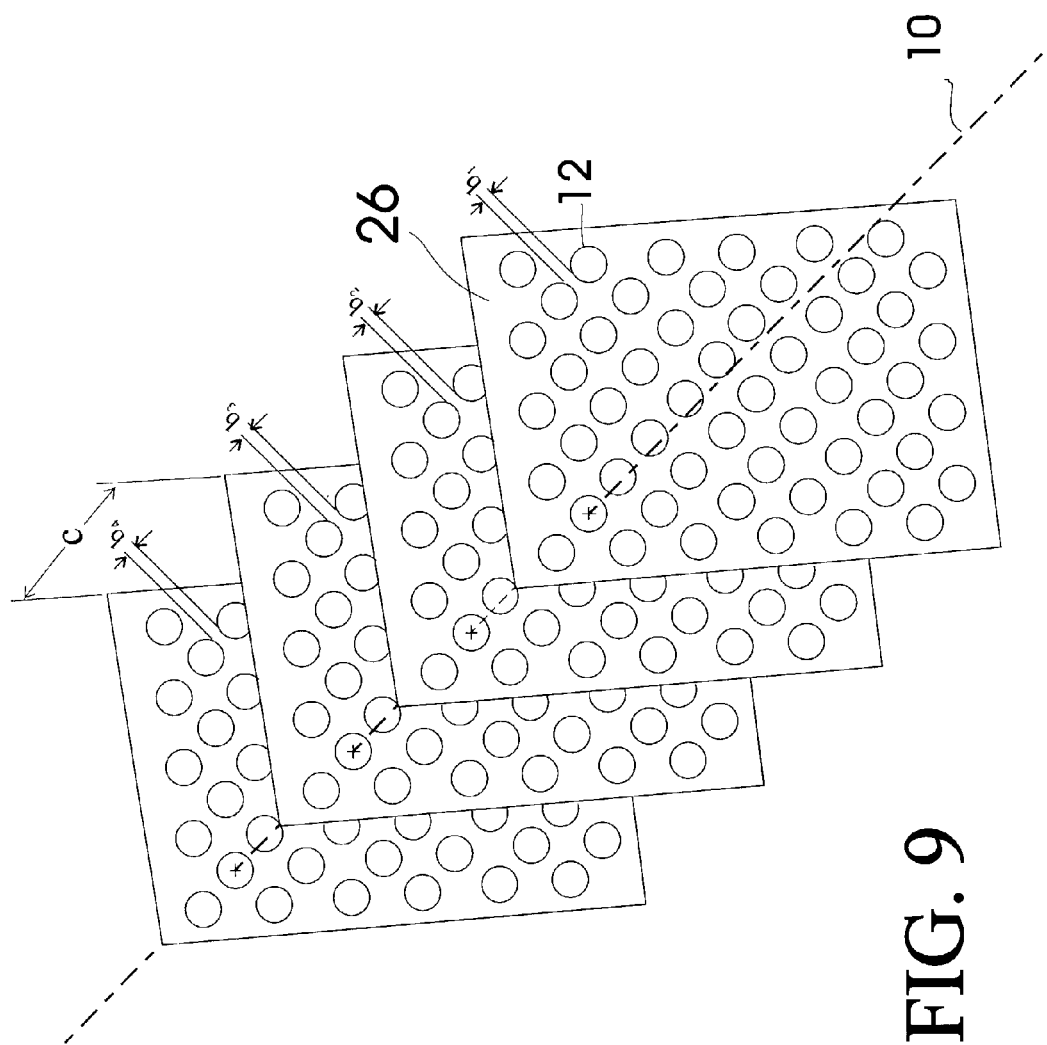
FIG. 9 shows an oblique view of stacked multiple unit-lens arrays on planar sheets to form a 3-D lens array.

This is the number of unit lenses for only one of the compound refractive lenses that form the inverting and erecting 3-D lens arrays (e.g. 18 and 22 respectively in FIG. 4). The number of lenses per unit area (in units of r) in the sheet of Kapton (or other appropriate lens material) is shown in FIG. 9 is $N_a=1/9r_a^2$, where $r_a$ is the absorption radius of the unit lens. This calculation assumes that the minimum spacing b between lenses is approximately $r_e$ and that the mechanical aperture has been designed to be $r_e=r_a$. However, as discussed above the spacing between lenses can be larger and is governed by the principle that one wishes to have uniform brightness across the erected image. The spacing between the lenses b is $$b \approx 2\left(2\frac{o}{l} - 1\right)r_a,$$

where again we are assuming that the effective aperture is given by the absorption aperture, $r_e \approx r_a$. The total number of unit lenses in a sheet is $N_y N_z = N_a A$, where A is the area of the 3-D lens arrays which is determined approximately by the area of the source or the area of the object that we wish to image. The total number of unit lenses per 3-D array is $N_t=N_x N_y N_z=N_x N_a A$. A large variation in this number of unit lenses can be tolerated without undue change in the optical system.

3. Methods of Fabrication for X-ray Lenses

To make fabrications easy and reduce cost, unit lenses can be mass-produced on single sheets of appropriate material such as Kapton or aluminum. This is shown in FIG. 9. Other more expensive materials can be used such as Be or Li. These latter materials are somewhat more difficult to use, but give larger absorption apertures. The unit lenses 12 are compression molded onto thin sheets of Kapton 26. These identical thin sheets are then stacked uniformly such that the unit lenses from each sheet are aligned with their identically positioned lens on the previous sheet such that they have a common optical axis 10. The accuracy of the alignment is such that the random variance $\sigma_t^2$ of the displacement $t_1$ off the average optical axis of the unit lenses forming the compound refractive lens is less than the absorption radius of the compound refractive lens formed by each stack of unit lenses. The unit lenses on the thin sheets are arranged diagonally by approximately 3 absorption radii, $r_a$, between centers. This gives a distance of approximately one absorption radius between unit lenses. Other suitable spacing can be used. If a thick lens design is needed (for very short focal lengths) then the spacing between the lenses $b_1, b_2, b_3, \ldots b_n$ should vary following equation (15). These spacing depend upon the field of view of the individual CRLs that compose the array and the desired magnification as governed by equation (15).

Dies for compression molding or de-bossing (or embossing) can be fabricated using lithographic, gray scale or MEMS fabrication techniques now used for visible optics. These techniques can be used to fabricate these lenses directly, but it is more expensive. Gray scale fabrication techniques have been used by companies to fabricate optical concave lenses with dimension as small as 15 microns across for each unit lens. Gray scale optics can be fabricated on Silicon, fused silica and plastics. All of which can be used in x-ray compound refractive lenses. However, the best material would be the plastic Kapton or polyamide, which has been use to fabricate single compound refractive lenses by Piestrup et al "Two-dimensional x-ray focusing from compound lenses made of plastic," Review of Scientific Instruments, 71, 4375 (2000). Lens array in sheets of Kapton as in FIG. 9 can be fabricated using these compression molding or de-bossing (or embossing) techniques using molds fabricated using the gray scale technique. Gray scale visible optics are currently being provided in production quantities by various companies in the US. These optics would be excellent for x-ray optics where a large number of unit lenses are required. These visible optics would be modified to make them extremely thin to reduce x-ray absorption and, hence, to maximize x-ray transmission through the entire 3-D lens array.

Figure 10:
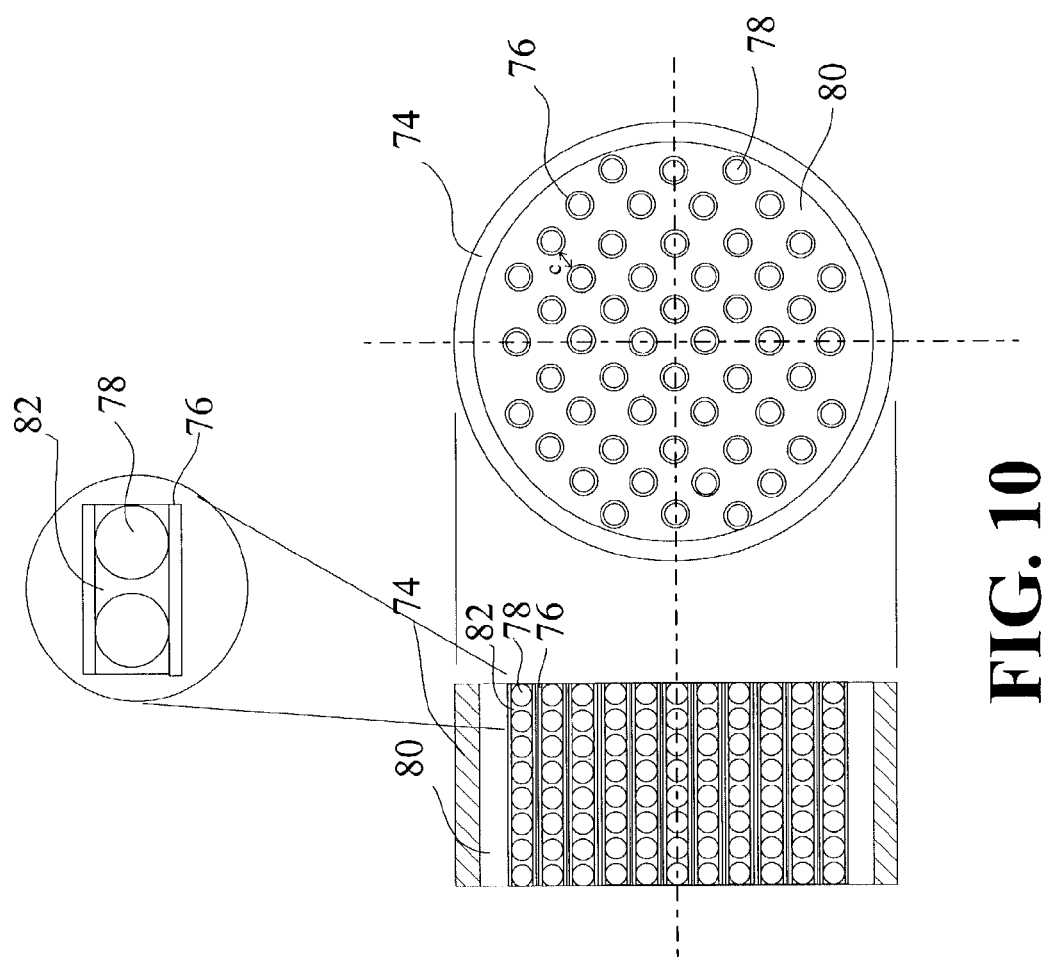
FIG. 10 shows three views of capillaries stacked together with bubble lenses inside forming a 3-D lens array.

Another inexpensive method of fabrication for large arrays of lenses is shown in FIG. 10, where a axial and side view of a single 3-D lens array is presented. An exploded view is also included of two of the bubbles inside a single capillary. The method uses bubbles 78 inside of capillaries 76 as was used by Dudchik et al. for a single capillary lens. In the 3-D array multi-capillaries 76 are placed suspended in epoxy filler 80 inside cylinder 74. These capillaries 76 are placed in an hexagonal array with spacing c between them. Epoxy 82 is also placed inside the capillaries 76 and, then bubbles 78 are injected. Bubble injection was done previously for single capillaries by Dudchik et al. Multiple injectors can simultaneously inject bubbles into the capillaries before the epoxy hardens. A long-glass microcapillary-injector needle is inserted in each capillary and air bubbles 78 are injected at a regular and well-regulated rate and air volume. Other materials including hollow spheres can replace the bubbles.

In summary, the embodiments of FIG. 6, 7 or 8 permit the magnification (or de-magnification) of an object's image. In these embodiments, the two compound refractive lens arrays 18 and 22 are different, having identical focal lengths but changing transverse spacing between the compound refractive lenses that compose the 3-D lens arrays. In other embodiments the focal lengths need not be identical. For the 3-D compound refractive lens systems to work, the nodal magnification must be equal to the lattice magnification.

4. Example Applications 4.1. Microscope and Telescopes

Using similar systems of 3-D arrays there are many applications using ordinary visible optics, which will now have direct analogies in x-ray and neutron optics systems. X-ray and neutron microscopes having large apertures can now be made, which can magnify small objects embedded in other materials. An x-ray telescope can now be fabricated for the collection and imaging of distant x-ray or neutron emitters. For explosive detection, characteristic-line emission from radioactive sources or from materials whose fluorescent emission has been activated can now be collected, detected and identified from large distances from these sources.

These embodiments can be used, for example, for x-ray lithography in the production of integrated circuits, and for magnification of breast tissue for the detection of cancer. Medical, industrial, and scientific imaging can be done with these lens arrays. Visible optic analogues from x-ray and neutron applications can be done using the 3-D lens arrays replacing single optical lenses. Thus, many applications will be apparent to those skilled in the art.

4.2. Mammography

Figure 11:
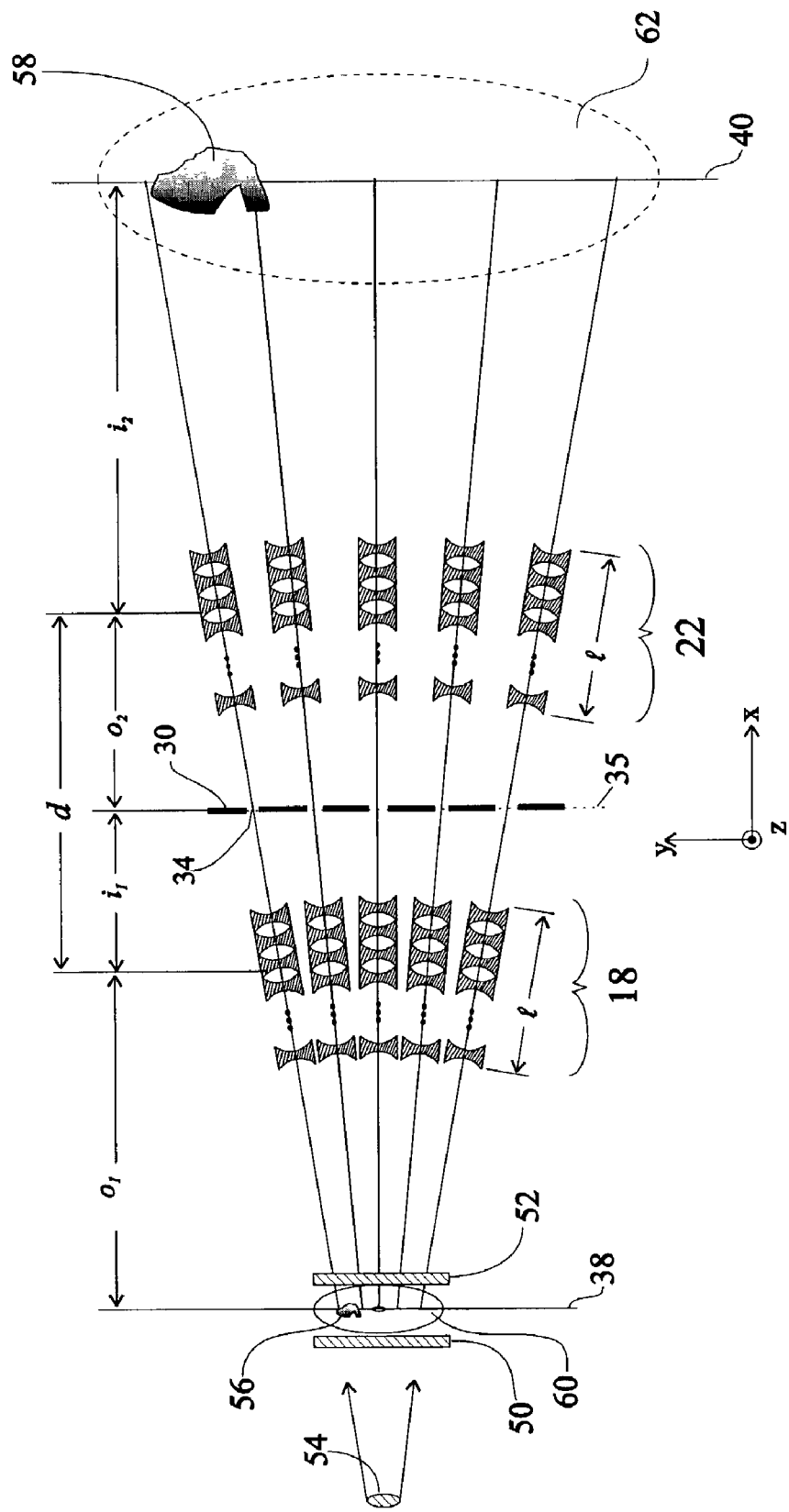
FIG. 11 shows a medical imaging-magnification system for mammography in the detection of carcinoma and cancer.

In FIG. 11 we show an apparatus that is used to produce an enlarged image of breast tissue for the detection of cancer. This apparatus is meant to replace conventional mammography systems that only give projection imaging of the breast. Conventional screen-film mammography is a critical diagnostic procedure in the fight against breast cancer—the second leading cause of death among women in the U.S. Even under well-managed conditions, mammography may fail to detect 11% to 15% of cancers. Only about one of three women referred for excisional biopsy is diagnosed with cancer. A successful alternative procedure that is both non-invasive and efficacious for these referred women would be an important breakthrough. The apparatus of FIG. 9 would produce larger images of higher resolution, improving efficacy.

As in the case of FIG. 6, 7 or 8, the inverting 3-D array 18 and the erecting 3-D array 22 form with the array of apertures 30 a microscope capable of imaging the entire breast 60. The spacing and positioning of the 3-D lens arrays are given by equation (12) or (15). As before the lattice magnification must be equal to the nodal magnification. An inverted intermediate image is formed at the aperture 37, which is then erected to form a magnified image at 58.

As with most mammography systems, the breast is compressed between two compression plates 50 and 52 in order to minimize the thickness of the breast and to reduce the overall x-ray attenuation through the breast 60. An appropriate x-ray source 54 illuminates the compressed breast 60.

In this embodiment, the x-ray source made to be of narrow bandwidth by using a Mo k-edge filter and Mo-anode material in the x-ray source. This reduces the bandwidth such that the chromatic aberrations of the microscope lens system do not reduce the resolution of the microscope appreciably. The compound refractive lenses are highly chromatic, having their focal lengths change appreciably with x-ray wavelength. As one skilled in the art knows, other techniques for narrowing the bandwidth are possible and other sources of x-rays are possible. These include the use of a compound refractive lens with an aperture or iris as discussed in U.S. Patent submission of H. R. Beguiristain, M. A. Piestrup, R. H. Pantell, "Methods of Imaging, Focusing and Conditioning Neutrons,"(submitted Sep. 27, 2001).

The mammography microscope of FIG. 11 will give a cross-sectional image of the breast across the object plane 40. For a properly designed lenses system, the lenses will have a depth of focus (as in the case of an optical microscope). Objects outside of this depth of focus will not be in focus at the image plane 40. In FIG. 11 we show a carcinoma 56, whose magnified image 58 is shown. The magnification of the image will permit Radiologist to see more accurately and clearly breast carcinoma and, thus, diagnose breast cancer earlier and more efficiently.

4.3. Lithography

At present the use of soft-x-ray radiation for the production of integrated circuits has been slowed by the lack of an inexpensive x-ray source and the inability to reduce the mask image of integrated circuit by any sort of x-ray optics. For the latter problem, only contact prints are made give a one-to-one image of the mask. Thus, the dimensions of the circuit pattern on the exposed wafer are the same as the dimensions on the mask. This requires a very expensive mask with circuit pattern to be fabricated.

Figure 12:
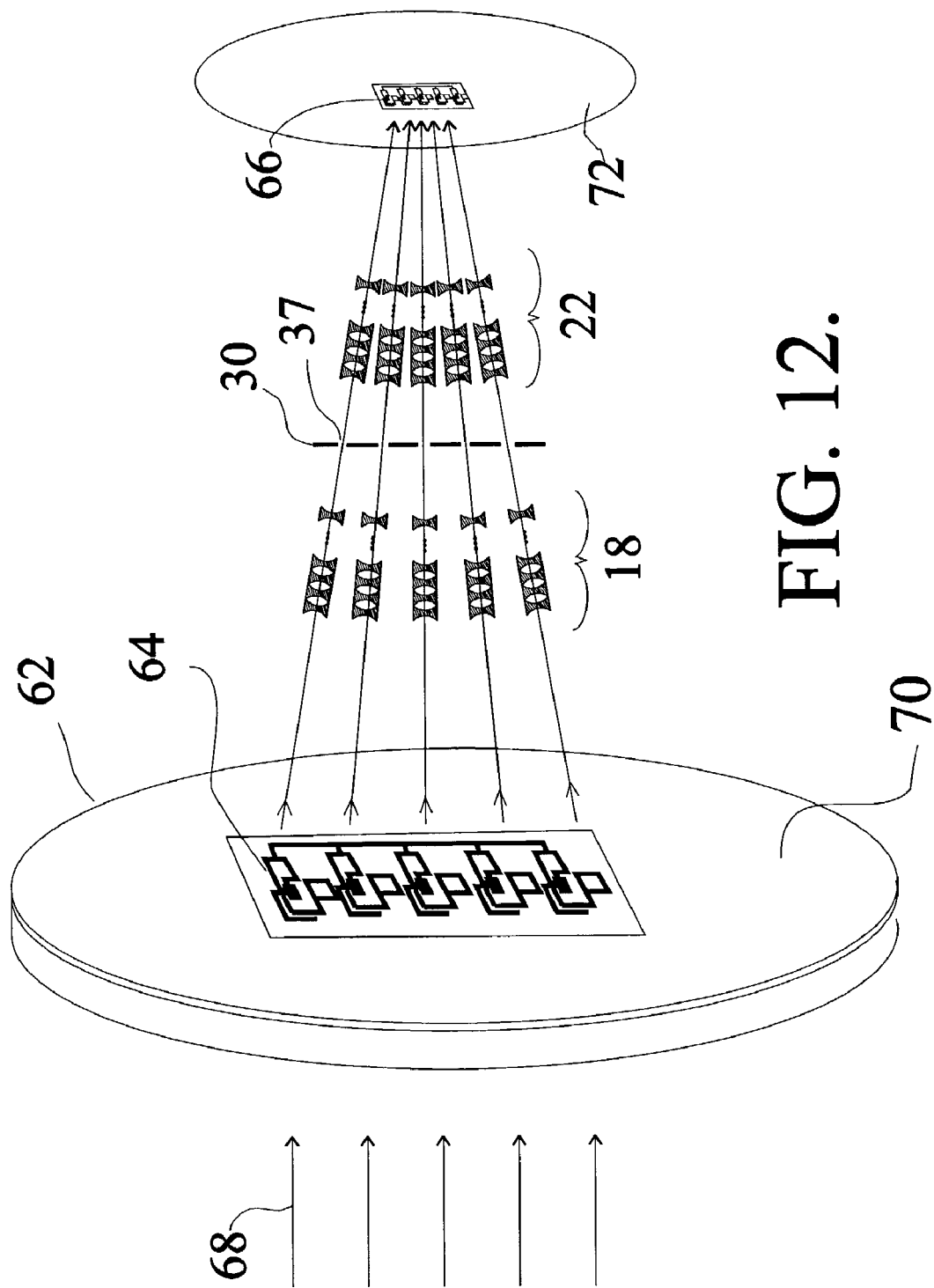
FIG. 12 shows an image-reduction system for soft x-ray lithography for the production of integrated circuits.

In visible-light and UV lithography, ordinary lenses can be used to reduce the image on the exposed photoresist-coated silicon wafer. The apparatus of FIG. 12 shows an image reduction apparatus using the methods of FIG. 5 or 6. The inverting 3-D array 18 and the erecting 3-D array 22 forms with the array of apertures 30 an image reduction lens system capable of imaging a circuit pattern 64 on to a silicon wafer 72 forming an reduced image of the circuit pattern 66. As before, an intermediate, inverted image 34 is formed in the aperture 37. The soft x-rays 68 pass through a thin minimally absorbing membrane 70, which supports a maximal absorbing circuit pattern 64 (forming a Mask 62), whose image 66 is projected and reduced onto a resist-coated silicon wafer 72. The circuit pattern image 66 exposes the photoresist so that further processing and etching of the silicon can take place. The image 66 is reduced so that higher density circuits can be manufactured. A narrow-bandwidth soft-x-ray source is used whose photon energy is near the region of maximum absorption for the photoresist and where the mask 62 furnishes the most contrast. This photon energy is usually just below 1.6 keV. A synchrotron radiator with monochromator can furnish x-rays of this energy. As one skilled in the art knows, other sources of x-rays are possible including rotating anode x-ray tubes, transition radiation and other novel sources of x-rays. These sources can be monochromatized by using a collecting compound refractive lens and an aperture {see again example, H. R. Beguiristain, M. A. Piestrup, R. H. Pantell, "Methods of Imaging, Focusing and Conditioning Neutrons, "(US patent submission Sep. 27, 2001)}.

4.4. Radioactive Source Detection

Three-dimensional (3-D) arrays can be used for collection of x-ray emitted from radioactive sources that may be distant or weak. The arrays can be large enough to collect sufficient characteristic x-rays for the identification of the emitting source. For example, such an apparatus could be used for the identification of nuclear material.

Figure 13:
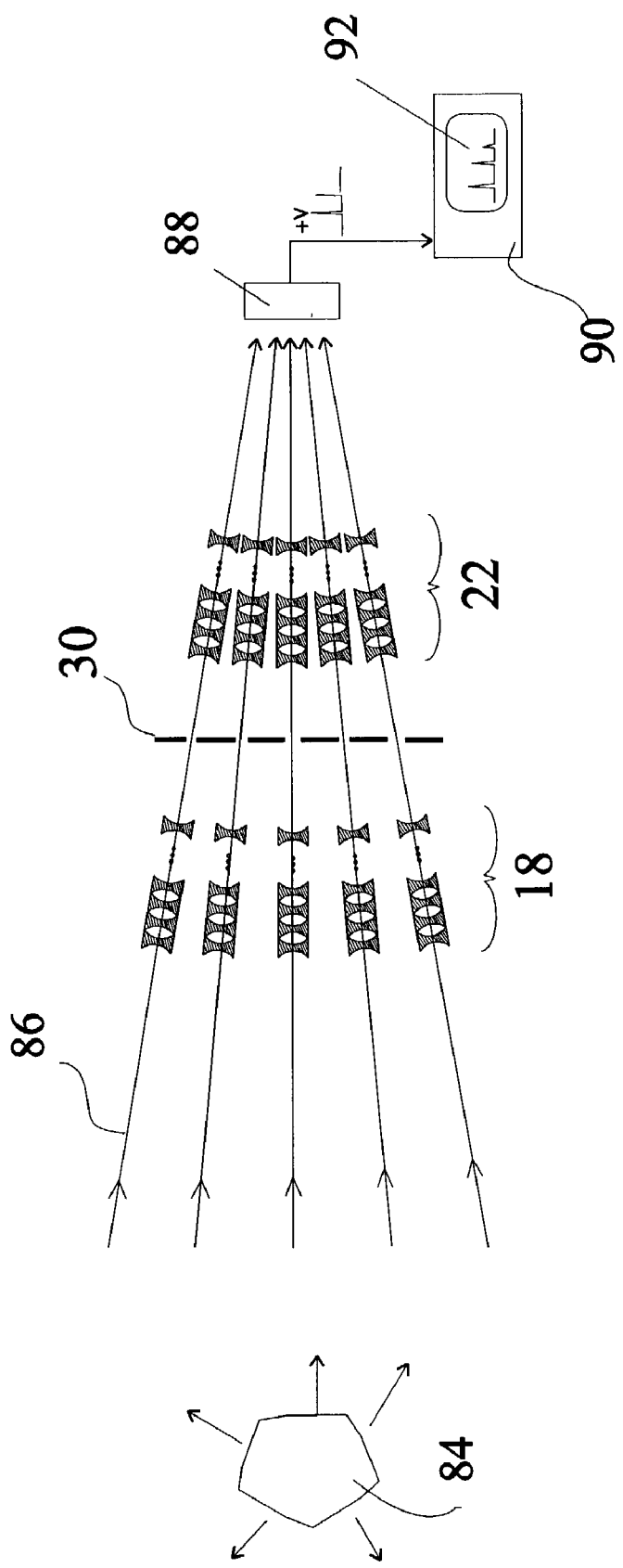
FIG. 13 shows a collection and imaging system for the detection of weak and/or distant radioactive sources.

An embodiment of the apparatus is shown in FIG. 13. As in the case of FIG. 6, 7 or 8, the inverting 3-D array 18 and the erecting 3-D array 22 form with the array of apertures 30 a telescope capable of collection and imaging the distant source of x-rays 84 on to a SiLi x-ray detector 88 which produces voltage pulses that are proportional to the height of the x-ray energies. The pulses are displayed on a Pulse Height Analyzer (PHA) 90 which display the x-ray spectrum 92. The spacing and positioning of the 3-D lens arrays are given by equation (12) or (15). As before the lattice magnification must be equal to the nodal magnification. The inverting 3-D array 18 and the erecting 3-D array form a telescope capable of collecting the x-ray emission 86 and imaging the source 84 on the detector 88. Both spatial and/or spectral information can be obtained from such an arrangement depending upon the detectors ability to give both positional and photon energy information.

Figure 14:
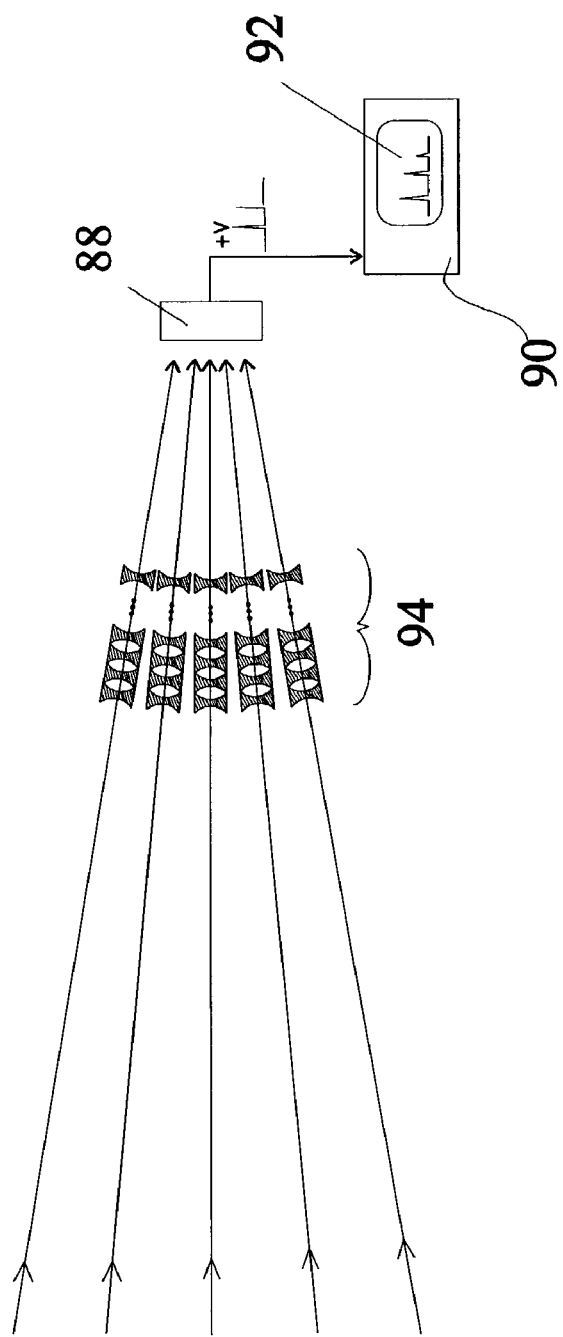
FIG. 14 shows a collection system for the detection of weak and/or distant radioactive sources.
Figure 14:
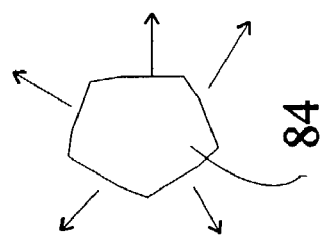

A single 3-D array can be used to collect X-ray on to a single detector. This can be used to improve the collection efficiency of the detector. In this case the array can act like a fly's eye in that multiple partial images will be presented at the image plane. This is shown in FIG. 14, wherein a 3-D array of unit lenses 94 are used. As before this said array is composed of a 2-D array of compound refractive lenses. The unit lenses are spaced horizontally such that the distances $b_1$, $b_2$, $b_3$, ... $b_n$ between lenses, as shown in FIG. 9, continuously increase as the distance from the detector increases. The divergence between the CRLs is such that the field of views of the lenses just overlaps. The detector 88 is a distance f from the 3-D array 94, if the x-ray source 84 is at a very large distance from the imaging system. As before, f is the focal length of one of the CRLs. If the x-ray source 84 is closer, then the distances between the various components follows the lens equation (7). In this embodiment, a SiLi x-ray detector 88 is used which produces voltage pulses that are proportional to the height of the x-ray energies. The pulses are displayed on a Pulse Height Analyzer (PHA) 90 which display the x-ray spectrum 92.

What is claimed is:

1. A lens system for imaging radiation that is x-rays or neutrons comprising:

a first plurality of compound refractive lenses, each compound refractive lens having an optic axis and configured to image a part of an object plane that intersects its optic axis, said plurality of compound refractive lenses arranged in a two-dimensional mosaic such that each compound refractive lens is oriented so as to receive radiation from a different part of said object plane, with each compound refractive lens providing a separate radiation path from that object plane, said two-dimensional mosaic hereinafter called the inverting mosaic;

wherein each of said compound refractive lenses has an index of refraction of less than 1 for said radiation.

2. The lens system of claim 1 wherein each of said plurality of compound refractive lenses is apertured so as to also receive radiation from at least a portion of the same part of said object plane as at least one other compound refractive lens among said first plurality of compound refractive lenses.

3. The lens system of claim 1 wherein each of said compound refractive lenses comprises a material transparent to x-rays.

4. The lens system of claim 1 wherein each of said compound refractive lenses comprises a material transparent to neutrons.

5. The lens system of claim 1 wherein each of said compound refractive lenses comprises a plurality of unit lens arranged along its individual optic axis, and wherein said unit lenses of different compound refractive lenses are laterally adjacent and are also arranged to form a two dimensional mosaic.

6. The lens system of claim 1 further comprising a second plurality of compound refractive lenses, has an index of refraction of less than 1 for said radiation and wherein each of said second plurality of compound refractive lenses has an optic axis that is aligned with the optic axis of one of said first plurality of compound refractive lenses.

7. The lens system of claim 6 wherein each of said first plurality of compound refractive lenses provides an inverted image of said different parts of said object plane.

8. The lens system of claim 7 wherein each of said second plurality of compound refractive lenses that is aligned with a compound refractive lens of said first plurality of compound refractive lenses is spaced apart from said compound refractive lens of said first plurality of compound refractive lens and erects the inverted image provided by the compound refractive lens of the first plurality of compound refractive lenses with which it is aligned.

9. The lens system of claim 8 wherein said second plurality of compound refractive lenses provides an erect image of that portion of the object plane from which said first plurality of compound refractive lenses receives radiation.

10. The lens system of claim 7 wherein among said compound refractive lenses of said first plurality of compound refractive lenses said lenses provide overlapping inverted images of said different parts of said object plane.

11. The lens system of claim 10 wherein each of said second plurality of compound refractive lenses that is aligned with a compound refractive lens of said first plurality of compound refractive lenses erects the inverted image provided by the compound refractive lens of the first plurality of compound refractive lenses with which it is aligned, said second plurality of compound refractive lenses being arranged in a two dimensional mosaic, hereinafter called the erecting mosaic.

12. The lens system of claim 11 further comprising a two dimensional surface for receiving radiation from said second plurality of compound refractive lenses, said surface having an image thereon of said part of the object plane imaged by said first plurality of said compound refractive lenses.

13. The lens system of claim 11 wherein said inverting mosaic has a magnification M and said erecting mosaic has a magnification N, such that said lens system has a total magnification of M times N.

14. The lens system of claim 11, wherein said compound refractive lenses comprising said inverting mosaic are identical to said compound refractive lenses comprising said erecting mosaic.

15. The lens system of claim 11, wherein said compound refractive lenses of said inverting mosaic have a focal length f1 and wherein said compound refracting lenses of said erecting mosaic have focal length of f2, and wherein f1 does not equal f2.

16. The lens system of claim 11, further comprising a detector positioned to receive radiation from said erecting mosaic.

17. The lens system of claim 5 further comprising a plurality of sheets, each sheet containing a plurality of said unit lenses with each unit lens having an optic axis perpendicular to said sheet, said sheets aligned parallel to each other such that each said unit lens is optically aligned with a corresponding unit lens on an adjacent sheet.

18. A system for imaging radiation from x-rays or neutrons comprising:
a first array of compound refractive lenses at least partially transparent to said radiation configured into a two dimensional mosaic, each compound refractive lens configured to image a portion of an object plane and to invert said image of said portion relative to said object plane;
a second array of compound refractive lenses also at least partially transparent to said radiation configured into a two dimensional mosaic, each compound refractive lens configured to receive radiation from a corresponding one of said compound refractive lenses in said first array, said second array configured for erecting said image of said portion inverted by said first array.

19. The system of claim 18 having a lattice magnification of M1, and wherein said first array and said second array together have a nodal magnification of Mn, wherein Mn equals M1.

20. The system of claim 19 further comprising a source of said radiation and a sample holder configured to hold a sample in a manner to be irradiated by said source, wherein said first and second arrays are oriented to receive radiation transmitted by the sample and to form an image thereof, and further comprising a detector oriented to receive said image.

21. The system of claim 18 further comprising a source of soft x-rays, a mask holder configured to hold a mask containing a circuit pattern to be irradiated by said source, wherein said first and second arrays are configured to receive radiation from said mask and to produce a reduced image of said circuit pattern.

22. The system of claim 18 further comprising a source of said radiation, a positioning apparatus configured to hold a human breast in a position to be irradiated by said source, and said first and second arrays oriented to receive radiation from the human breast.

23. The system of claim 18 further comprising an aperture array located between said first and second arrays said aperture array having a plurality of apertures, each aperture aligned with one of said compound refractive lenses.

24. The system of claim 18 further comprising a plurality of aperture arrays located between said first and second arrays each of said aperture arrays having a plurality of apertures, each aperture aligned with one of said compound refractive lenses of said first and second arrays.

25. A method of producing an image of an object irradiated with neutrons or x-rays, comprising the steps of receiving radiation from said object with a linear array of compound refractive lenses, said step of receiving radiation comprises translating said linear array of compound refractive lenses relative to said object in a direction orthogonal to said linear array, so as to receive said radiation from said object in a time ordered manner from different parts of said object.

26. A system for imaging an object plane comprising a linear array of compound refractive lenses having a linear axis along which said compound refractive lenses are arranged, and a translator coupled to said linear array that is configured to cause relative motion of said linear array relative to said object plane that is in a direction orthogonal to the linear axis of said linear array;
wherein each of said compound refractive lenses comprises a material transparent to a form of radiation selected from the group consisting of x-rays and neutrons; and
wherein each of said compound refractive lenses has an index of refraction of less than 1 for the selected form of radiation.

* * * * *